United States Patent
Yoon

[19]
[11] Patent Number: 5,810,845
[45] Date of Patent: Sep. 22, 1998

[54] LIGATING INSTRUMENT WITH MULTIPLE LOOP LIGATURE SUPPLY AND METHODS THEREFOR

[76] Inventor: InBae Yoon, 2101 Highland Ridge Dr., Phoenix, Md. 21131

[21] Appl. No.: 694,385

[22] Filed: Aug. 8, 1996

Related U.S. Application Data

[63] Continuation-in-part of Ser. No. 533,504, Sep. 25, 1995, Pat. No. 5,704,943.

[51] Int. Cl.$^6$ .................................................... A61B 17/10
[52] U.S. Cl. .......................... 606/139; 606/140; 606/142; 606/144; 606/148; 606/151
[58] Field of Search ..................................... 606/139, 144, 606/148, 140, 145, 151

[56] References Cited

U.S. PATENT DOCUMENTS

| | | |
|---|---|---|
| 2,012,776 | 5/1935 | Roeder . |
| 2,227,270 | 1/1940 | Moore . |
| 2,610,631 | 11/1952 | Calicchio . |
| 2,856,933 | 1/1958 | Hildebrand et al. . |
| 3,033,204 | 5/1962 | Wood . |
| 3,580,256 | 5/1971 | Wilkinson . |
| 3,871,379 | 3/1975 | Clarke . |
| 4,018,229 | 4/1977 | Komiya . |
| 4,177,813 | 12/1979 | Miller et al. . |
| 4,235,238 | 11/1980 | Ogiu et al. . |
| 4,387,489 | 6/1983 | Dudek . |
| 5,100,415 | 3/1992 | Hayhurst . |
| 5,100,418 | 3/1992 | Yoon et al. ............................. 606/139 |
| 5,133,723 | 7/1992 | Li et al. . |
| 5,160,339 | 11/1992 | Chen et al. . |
| 5,176,691 | 1/1993 | Pierce . |
| 5,196,022 | 3/1993 | Bilweis . |
| 5,236,434 | 8/1993 | Callicrate . |
| 5,242,459 | 9/1993 | Buelna . |
| 5,281,238 | 1/1994 | Chin et al. . |
| 5,282,809 | 2/1994 | Kammerer et al. . |
| 5,290,284 | 3/1994 | Adair . |
| 5,300,078 | 4/1994 | Buelna . |
| 5,306,280 | 4/1994 | Bregen et al. . |
| 5,312,423 | 5/1994 | Rosenbluth et al. . |
| 5,318,578 | 6/1994 | Hasson . |

(List continued on next page.)

FOREIGN PATENT DOCUMENTS 0477020  3/1992  European Pat. Off. .

OTHER PUBLICATIONS

PortSaver PercLoop by Advanced Surgical, Inc. Features & Benefits and Specifications Berry & Kohn's Introduction to Operating Room Technique, McGraw–Hill Book Company.

*Primary Examiner*—Michael Buiz
*Assistant Examiner*—Tina T. D. Pham

[57] ABSTRACT

A ligating instrument includes an instrument body and a ligature supply disposed in the instrument body. The ligature supply includes a plurality of preformed, contractible ligature loops of filamentous ligature material, each ligature loop having a contractible loop segment and a knotting element movable along the ligature material in a direction to contract the loop segment around anatomical structure to form a ligature. The instrument body includes an actuator for sequentially, selectively deploying the ligature loops externally of the instrument body, an operating member for moving the knotting elements of the externally deployed ligature loops in the direction to contract the loop segments of the externally deployed ligature loops around anatomical structure to form ligatures and a handle for operating the actuator and the operating member. A method of forming ligatures in anatomical structure at an internal operative site in a body includes the steps of introducing a distal end of an elongate member of a ligating instrument at the internal operative site, moving the distal end from a closed position to an open position, moving an actuator of the ligating instrument to distally advance a plurality of preformed, contractible ligature loops of filamentous ligature material within a lumen of the elongate member to move one of the ligature loops externally of the distal end in the open position, positioning the external ligature loop around anatomical structure and moving a knotting element of the external ligature loop to contract the external ligature loop around the anatomical structure to form a ligature.

42 Claims, 8 Drawing Sheets

U.S. PATENT DOCUMENTS

| | | |
|---|---|---|
| 5,320,629 | 6/1994 | Noda et al. . |
| 5,330,491 | 7/1994 | Walker et al. . |
| 5,334,199 | 8/1994 | Yoon . |
| 5,336,231 | 8/1994 | Adair . |
| 5,383,882 | 1/1995 | Buess et al. . |
| 5,383,905 | 1/1995 | Golds et al. . |
| 5,403,330 | 4/1995 | Tuason . |
| 5,403,331 | 4/1995 | Chesterfield et al. . |
| 5,423,837 | 6/1995 | Mericle et al. . |
| 5,445,167 | 8/1995 | Yoon et al. . |
| 5,454,820 | 10/1995 | Kammerer et al. . |
| 5,562,689 | 10/1996 | Green et al. .................... 606/151 |

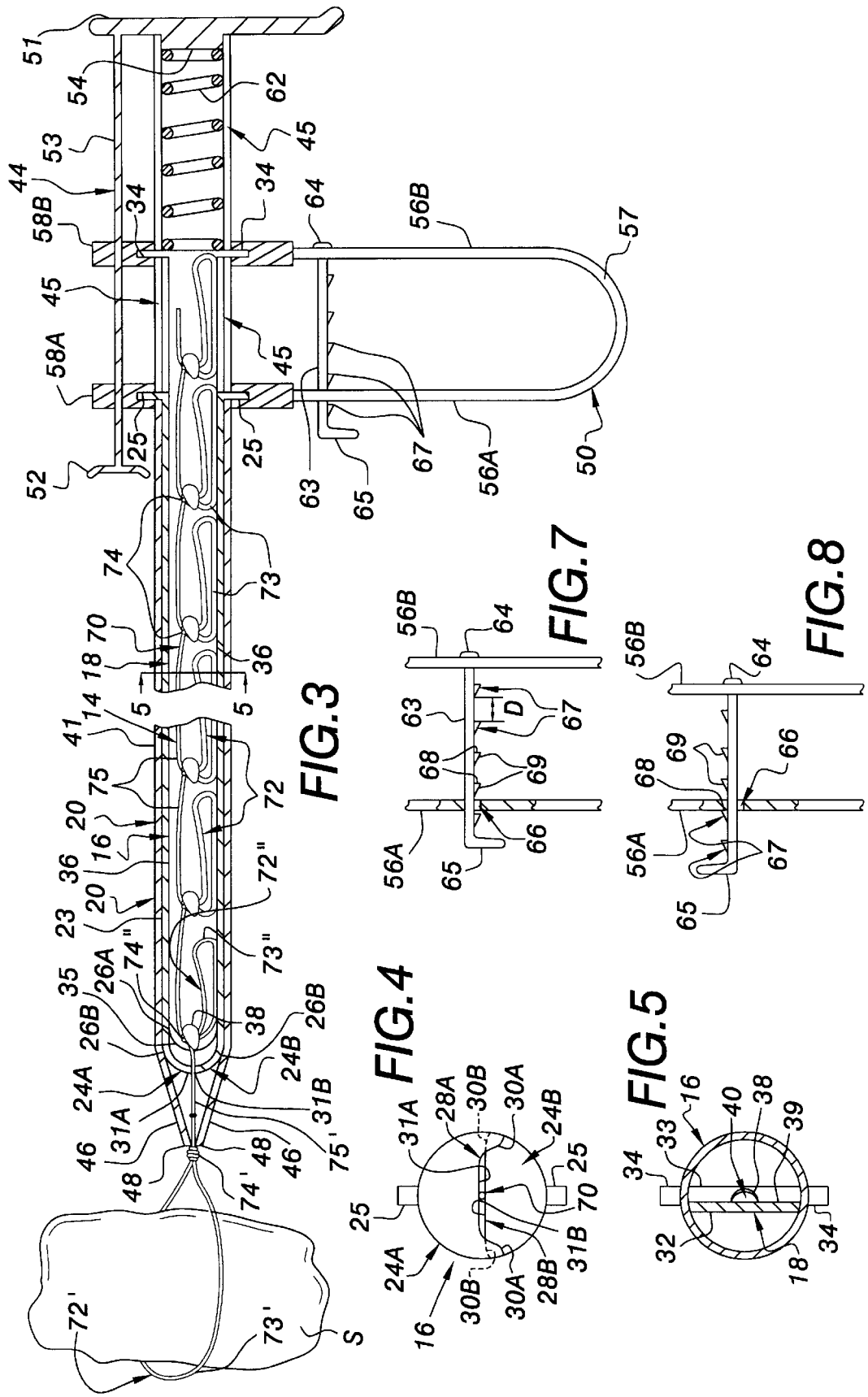

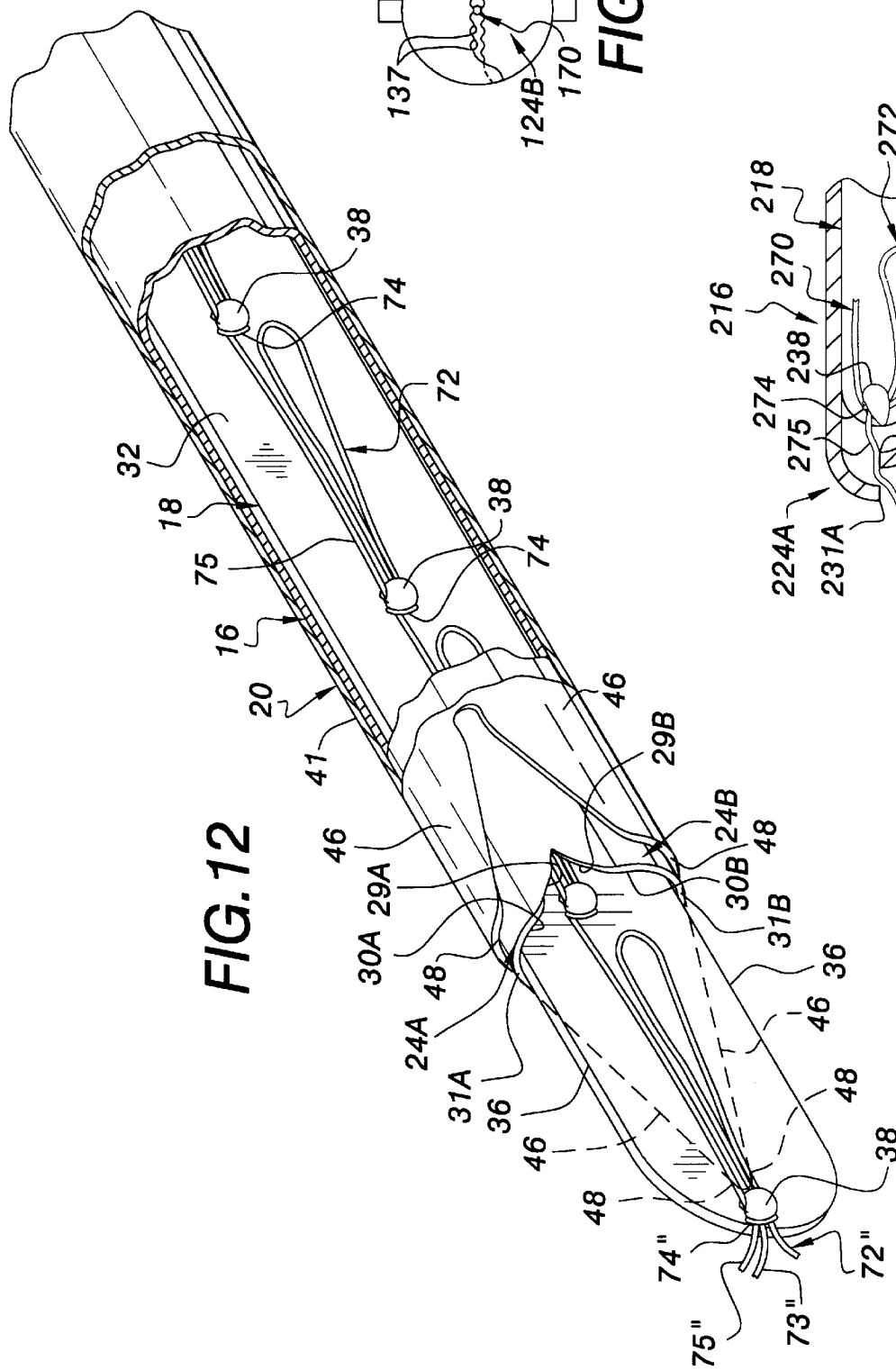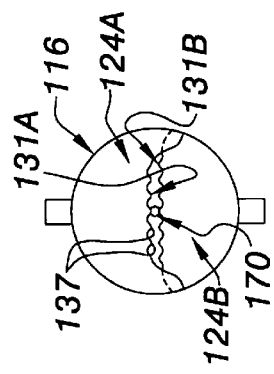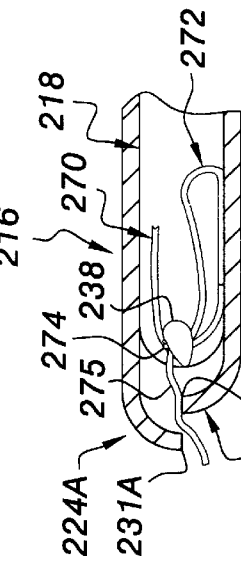

LIGATING INSTRUMENT WITH MULTIPLE LOOP LIGATURE SUPPLY AND METHODS THEREFOR

CROSS-REFERENCE TO RELATED PATENT APPLICATIONS

This application is a continuation-in-part of prior application Ser. No. 08/533,504 filed Sep. 25, 1995, now U.S. Pat. No. 5,704,943, the disclosure of which is incorporated herein by reference.

BACKGROUND OF THE INVENTION

1. Field of the Invention

The present invention pertains to ligating instruments and, more particularly, to ligating instruments operable with one hand for use in endoscopic and non-endoscopic operative procedures and to methods therefor.

2. Discussion of the Prior Art

Closed or endoscopic operative procedures, also known as least-invasive procedures, have become extremely popular for use in many areas such as laparoscopy (pelviscopy), gastroentroscopy, laryngobronchoscopy and arthroscopy, for example. In endoscopic operative procedures, access to an internal operative site in the body is gained through a relatively narrow or small size endoscopic portal establishing communication with the internal operative site from externally of the body. Accordingly, various instruments can be introduced at the operative site via the portal without the need for a skin incision of substantial size as is typically required for open operative procedures. Endoscopic procedures provide many benefits over open procedures including minimal invasiveness and trauma, fewer complications, shorter wound healing times, less patient discomfort, shorter hospitalization and rehabilitation times, cost savings and the ability to perform surgery without general anesthesia and in non-hospital or out-patient settings.

Ligating or tying anatomical tissue or organ structure is a time consuming and tedious part of both endoscopic and non-endoscopic operative procedures due to the difficulty involved in tying or applying an occluding ligature to anatomical structure as is desirable and/or necessary in many various procedures. Ligating anatomical structure is particularly difficult in endoscopic procedures due to the constraints on access to the operative site, the limited room for maneuverability at the operative site and the procedural or operational complexity required of many conventional endoscopic ligating instruments. Accordingly, the advantages of endoscopic procedures are sometimes outweighed by the disadvantages caused by the increased difficulty to ligate or tie and the increased length of time required to perform endoscopic procedures where such time is significantly extended due to the time required for ligation or tying.

Because endoscopic procedures are preferred over open procedures, much effort has been spent to develop instruments and techniques for facilitating tissue ligation. One technique involves the use of a ligating device, such as the Endoloop™ manufactured by Ethicon Endo-Surgery, Inc. Various other ligating devices or instruments have been proposed, as exemplified by U.S. Pat. No. 5,486,186 to Yoon, U.S. Pat. No. 5,383,882 to Buess et al, U.S. Pat. No. 5,336,231 to Adair, U.S. Pat. No. 5,334,199 to Yoon, U.S. Pat. No. 5,300,078 to Buelna, U.S. Pat. No. 5,290,284 to Adair, U.S. Pat. No. 5,281,238 to Chin et al, U.S. Pat. No. 5,242,459 to Buelna, U.S. Pat. No. 5,236,434 to Callicrate and U.S. Pat. No. 2,610,631 to Calicchio.

Many presently available ligating devices, instruments and procedures have various disadvantages including structural and operational complexity, tedious, difficult and time consuming procedural steps, the need for two-handed operation, the inability to sense or "feel" desired ligature tension and the inability to form multiple ligatures or ties without withdrawing the ligating devices or instruments from the operative site.

SUMMARY OF THE INVENTION

Accordingly, it is a primary object of the present invention to overcome the disadvantages of prior art ligating devices, instruments and procedures.

Another object of the present invention is to provide a simplified ligating instrument for forming a plurality of ligatures at an internal operative site in the body without withdrawal of the ligating instrument from the body.

A further object of the present invention is to provide a ligating instrument including an elongate instrument body and a ligature supply including a plurality of preformed, contractible ligature loops of filamentous ligature material disposed in the instrument body, the instrument body including a deployer for sequentially deploying the ligature loops externally of the instrument body for use in forming ligatures.

An additional object of the present invention is to hold a ligature supply of a ligating instrument with an engaging member of the ligating instrument as a knotting element of an externally deployed ligature loop of the ligature supply is moved to contract the externally deployed ligature loop around anatomical structure to form a ligature.

The present invention has as a further object to utilize one hand to operate a handle of a ligating instrument to retract an operating member and to extend a deployer of the ligating instrument relative to an engaging member of the ligating instrument to sequentially deploy a ligature loop externally of the operating member.

A still further object of the present invention is to move a distal end of an operating member of a ligating instrument from a contracted position to an expanded position in response to retraction of the operating member and to move a distal end of an engaging member of the ligature supply from a grasping position to a non-grasping position in response to extension of a deployer of the ligating instrument to externally deploy a ligature loop of the operating member.

It is also an object of the present invention to releasably engage a ligature supply with a deployer of a ligating instrument body such that the ligature supply is advanced by the deployer to deploy a ligature loop externally of the instrument body, to disengage the ligature supply from the deployer after the ligature loop has been deployed externally of the instrument body and to releasably reengage the ligature supply with the deployer to externally deploy another ligature loop.

Yet another object of the present invention is to hold a filamentous ligature supply of a ligating instrument with an engaging member of the ligating instrument as a knotting element of an externally deployed ligature loop of the ligature supply is moved to contract the externally deployed ligature loop around anatomical structure to form a ligature and to thereafter cut the ligature supply with the engaging member proximally of the ligature to sever the ligature from the remainder of the ligature supply.

Some of the advantages of the present invention are that ligating anatomical structure is facilitated in both endoscopic and non-endoscopic procedures, the ligating instrument is operable with a single hand to form a plurality of ligatures, various diverse ligature supplies can be coupled with the instrument body allowing an optimal ligature supply to be selected in accordance with procedural use, ligatures can be formed in anatomical structure with a desired tension as tactilely sensed by the surgeon, cutting of the ligature material proximally of the ligatures can be accomplished with the same instrument used to form the ligatures, and various functions or procedural steps normally requiring separate instruments can be performed utilizing a single instrument.

These and other objects, advantages and benefits are realized with the present invention as generally characterized in a ligating instrument including an instrument body and a ligature supply disposed within the instrument body. The instrument body comprises an elongate, hollow engaging member housing the ligature supply, an actuator or deployer disposed within the engaging member, an operating member receiving the engaging member and a handle for operating the actuator and the operating member. The engaging member has a distal end movable from a closed position to an open position in response to longitudinal distal movement of the actuator from a neutral longitudinal position to a deployed longitudinal position and movable from the open position back to the closed position in response to longitudinal proximal movement of the actuator from the deployed position to the neutral position. The actuator has a distal end disposed within the engaging member in the neutral position and disposed externally of the engaging member in the deployed position. The operating member is movable longitudinally, distally relative to the engaging member from an initial longitudinal position to an extended longitudinal position and is movable longitudinally, proximally relative to the engaging member from the extended position to the initial position. The operating member is movable longitudinally, proximally relative to the engaging member from the initial position to a retracted longitudinal position and is movable longitudinally, distally relative to the engaging member from the retracted position to the initial position. The operating member has a distal end disposed in a contracted position when the operating member is in the initial and extended positions and disposed in an expanded position when the operating member is in the retracted position. When the operating member is in the retracted position and the actuator is in the deployed position, the distal end of the actuator is disposed distally of the distal end of the operating member. The handle includes a hand grip for moving the actuator between the neutral and deployed positions and a finger grip for moving the operating member between the initial, extended and retracted positions with the hand grip and finger grip being operable by a single hand.

The ligature supply includes a plurality of preformed, contractible ligature loops of filamentous ligature material disposed in the engaging member and releasably engaged by the actuator. Each ligature loop includes a loop segment of the ligature material and a knotting element movable along the ligature material in a direction to contract the loop segment. The knotting elements are of a size preventing passage of the knotting elements and, therefore, the ligature loops, externally of the distal end of the engaging member when the distal end of the engaging member is in the closed position and permitting passage of the ligature loops externally of the distal end of the engaging member when the distal end of the engaging member is in the open position. The knotting elements are of a size preventing passage of the knotting elements and, therefore, the ligature loops, externally of the distal end of the operating member when the distal end of the operating member is in the contracted position and permitting passage of the ligature loops externally of the distal end of the operating member when the distal end of the operating member is in the expanded position.

When the operating member is in the retracted position with the distal end thereof in the expanded position, the actuator is moved to the deployed position to move the distal end of the engaging member from the closed position to the open position. Movement of the actuator to the deployed position causes the ligature supply, which is carried by the actuator, to be distally advanced relative to the engaging member such that one of the ligature loops passes externally of the open distal end of the engaging member and the expanded distal end of the operating member. When the actuator is moved from the deployed position back to the neutral position, the actuator is disengaged from the ligature supply causing the one ligature loop to remain externally of the instrument body. Movement of the actuator to the neutral position causes the distal end of the engaging member to return to the closed position, and the distal end of the engaging member in the closed position grasps the ligature material. When the operating member is moved from the retracted position back to the initial position, the distal end thereof returns to the contracted position and is disposed proximally of the knotting element of the one ligature loop. Movement of the operating member from the initial position toward the extended position causes the knotting element of the one ligature loop to be moved by the distal end of the operating member in the direction to contract the loop segment of the one ligature loop around anatomical structure to form a ligature. Further movement of the actuator to the deployed position, with the operating member in the retracted position causes the ligature supply to be releasably reengaged by the actuator for deployment of another ligature loop externally of the instrument body for use in forming another ligature.

According to a preferred embodiment, the ligature loops are connected to one another by connecting segments of the ligature material, and the connecting segment of the externally deployed ligature loop is grasped by the engaging member as the operating member moves the knotting element of the externally deployed ligature loop to contract the loop segment thereof around anatomical structure to form the ligature. Once the ligature has been formed with the externally deployed ligature loop, the connecting segment of the externally deployed ligature loop is cut with the engaging member to sever the ligature from the remainder of the ligature supply.

A method of forming ligatures in anatomical structure at an internal operative site in a body according to the present invention includes the steps of introducing a distal end of an elongate member of a ligating instrument at an internal operative site, moving the distal end from a contracted position to an expanded position, moving an actuator of the ligating instrument to distally advance a plurality of preformed, contractible ligature loops of filamentous ligature material within the elongate member to move one of the ligature loops externally of the distal end in the open position, positioning the external ligature loop around anatomical structure and moving a knotting element of the external ligature loop to contract the external ligature loop around the anatomical structure to form a ligature.

BRIEF DESCRIPTION OF THE DRAWINGS

FIG. 3 is a broken, side sectional view of the ligating instrument showing a ligature loop of the ligature supply deployed externally of the instrument body and positioned around anatomical structure to be ligated.

FIG. 4 is a distal end view of the engaging member of the ligating instrument.

FIG. 5 is a sectional view of the engaging member and the deployer of the ligating instrument taken along line 5—5 of FIG. 3.

FIG. 7 is a broken side view, partly in section, of the hand grip of the ligating instrument showing the hand grip in an unlocked position.

FIG. 8 is a broken side view, partly in section, of the hand grip of the ligating instrument showing the hand grip in a locked position.

FIG. 12 is a broken perspective view, partly in section, of a distal portion of the ligating instrument showing the next proximal ligature loop deployed externally of the instrument body for use in forming another ligature.

FIG. 13 is a distal end view of a modification of the engaging member.

FIG. 14 is a broken, side sectional view of another modification of the engaging member.

DESCRIPTION OF THE PREFERRED EMBODIMENT

Figure 1:
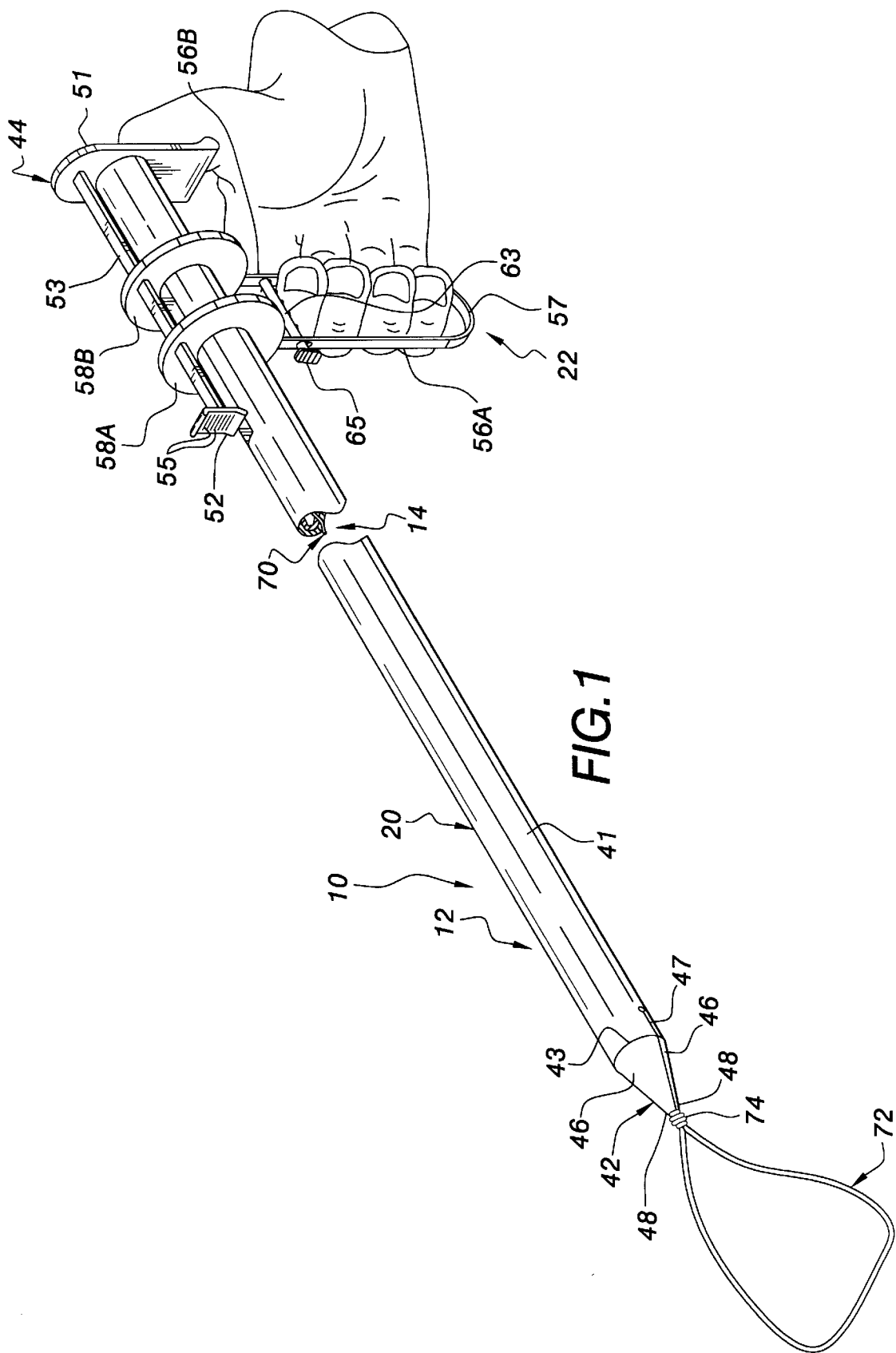
FIG. 1 is a broken perspective view of a ligating instrument according to the present invention.
Figure 2:
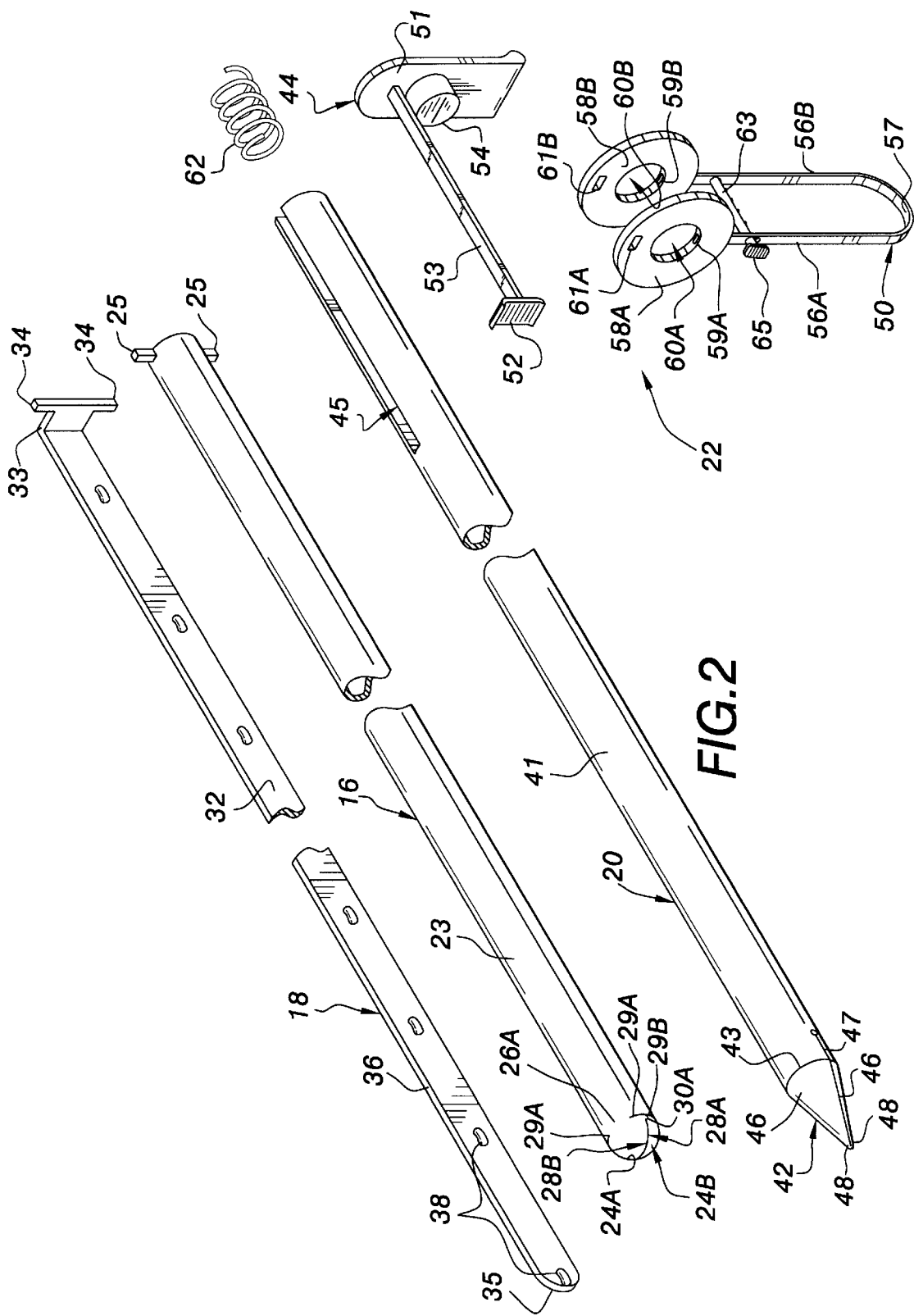
FIG. 2 is a broken, exploded perspective view of the instrument body of the ligating instrument.

A ligating instrument 10 according to the present invention is illustrated in FIG. 1 and includes an instrument body 12 and a multiple loop ligature supply 14 disposed or housed within the instrument body 12. The instrument body 12, as best illustrated in FIGS. 2 and 3, includes an elongate engaging member or jaw member 16, an elongate actuator or deployer 18 slidably disposed in engaging member 16, an operating member comprising a knotting element pusher or mover 20 receiving engaging member 16 and a handle 22 coupled with engaging member 16, actuator 18 and knotting element pusher 20. The engaging member 16 comprises a tubular or hollow elongate body 23 and a pair of opposed jaws or flaps 24A and 24B at a forward or distal end of the engaging member body 23. The engaging member body 23 is cylindrical in the case of engaging member 16 and terminates proximally at an open proximal end configured or provided with one or more transverse or radially extending flanges or ears 25 coupled with handle 22. Engaging member 16 includes two discrete transverse flanges 25 spaced 180° from one another about a longitudinal axis of engaging member 16, each flange 25 extending along a portion of the circumference or periphery of the cross-sectional configuration of the engaging member body 23. It should be appreciated, however, that any number of discrete, partial circumferential or partial peripheral transverse flanges suitable to attach the engaging member to the handle can be provided and that a flange extending entirely along the circumference or periphery of the cross-sectional configuration of the engaging member body can be provided instead of one or more partial circumferential or partial peripheral flanges. It should also be appreciated that the engaging member body does not have to be cylindrical and can have various non-circular cross-sectional configurations. Jaws 24A and 24B extend distally from the forward end of the engaging member body 23 and each jaw includes a curved, partial spherical wall merging with the forward end of the engaging member body 23 such that the jaws 24A and 24B together define a semi-spherical or substantially semi-spherical, rounded distal end for engaging member 16. The jaws 24A and 24B include pivot, joint or hinge segments 26A and 26B, respectively, merging with and pivotally, resiliently or flexibly connecting the jaws to the engaging member body 23. As shown in FIG. 3, hinge segments 26A and 26B are spaced 180° from one another about the longitudinal axis of the engaging member; and, in the case of engaging member 16, the hinge segments 26A and 26B are integral and unitary with the engaging member body 23. However, it should be appreciated that the jaws 24A and 24B can be pivotally or rotatably mounted to the engaging member body with separate hinge, pivot or joint structure, such as pivot pins, with or without hinge segments.

Jaws 24A and 24B together define a maximum, external jaw cross-section at the hinge segments 26A and 26B, and the maximum, external jaw cross-section is the same or substantially the same as the uniform external cross-section of the engaging member body 23. The external jaw cross-section tapers or diminishes in size from the hinge segments 26A and 26B in the distal direction. The curved walls defining jaws 24A and 24B, respectively, are of uniform or substantially uniform thickness to define a hollow interior for the jaws communicating with the lumen or hollow interior of the engaging member body 23. The engaging member 16 preferably has an external diameter or cross-sectional size to be closely received within knotting element pusher 20 while allowing the engaging member 16 and the knotting element pusher 20 to be moved longitudinally relative to one another.

Jaws 24A and 24B have jaw edges 28A and 28B, respectively, as best shown in FIGS. 2 and 4. Jaw edge 28A for jaw 24A includes a pair of rearward edge segments 29A, a pair of intermediate edge segments 30A extending distally from the rearward edge segments, respectively, and a forward edge segment 31A extending between the intermediate edge segments. Rearward edge segments 29A, which follow the periphery of the maximum, external jaw cross-section when the jaws are in a closed or grasping position as shown in FIGS. 2 and 4, are disposed at opposite sides of hinge segment 26A and have upper ends merging with a forward edge of the engaging member body 23 and lower ends merging with the intermediate edge segments 30A, respectively. With the jaws in the closed position, each intermediate edge segment 30A curves convexly from the corresponding rearward edge segment 29A to merge distally with forward edge segment 31A, which has an arcuate configuration. The forward edge segment 31A curves outwardly in the distal direction from the intermediate edge segments when the jaws are in the closed position such that a portion of the forward edge segment 31A centrally located between intermediate edge segments 30A defines a distal most end for jaw 24A. The intermediate edge segments 30A are sharpened to form cutting edges for cutting filamentous ligature material of ligature supply 14 as explained further below. Jaw edge 28B for jaw 24B includes rearward edge segments 29B, only one of which is visible in FIG. 2, intermediate edge segments 30B shown in FIG. 4 and a forward edge segment 31B. Jaw edge 28B is similar to jaw edge 28A except that intermediate edge segments 30B, which need not be sharpened, slope gently or are slightly concave between forward edge segment 31B and rearward edge segments 29B.

As shown in FIGS. 3 and 4, jaws 24A and 24B are disposed in the closed, grasping, holding or engaging position wherein forward edge segments 31A and 31B are slightly spaced or separated from one another to define a space, opening or passage therebetween for receiving a length of filamentous ligature material 70 of ligature supply 14, the space, opening or passage communicating with the hollow interior of the jaws. The distance between the forward edge segments 31A and 31B in the grasping position is sufficiently large to permit the length of filamentous ligature material 70 to pass therebetween while being frictionally held or grasped between forward edge segments 31A and 31B and is sufficiently small to prevent ligature loops of ligature supply 14 from passing therebetween as explained further below. Accordingly, the forward edge segments 31A and 31B define opposed grasping surfaces or edge segments for grasping or holding the length of filamentous ligature material 70. One or both of the forward edge segments 31A and 31B can be serrated, grooved, roughened, irregularly shaped or provided with protrusions, such as teeth, to enhance gripping of the length of ligature material between the jaws. In the grasping position, the intermediate edge segments 30A of jaw 24A overlap jaw 24B such that the intermediate edge segments 30B are disposed within jaw 24A. Accordingly, the sharpened intermediate edge segments 30A protrude from or are disposed slightly distally of jaw 24B such that the cutting edges formed thereby are in a position to cut the length of ligature material 70 disposed between the jaws when the instrument body 12 is pivoted, angled or tilted as explained further below. The forward edge segments 31A and 31B for jaws 24A and 24B, respectively, are non-overlapping in the grasping position. However, it should be appreciated that the forward edge segment of either one of the jaws can overlap the other of the jaws in the grasping position and that the cutting edges can be disposed on either or both of the jaws. It should also be appreciated that the forward edge segments of the jaws can be designed to contact one another when the ligature material does not pass therebetween, in which case the forward edge segments are separated from one another in the grasping position due to flexing of the jaws when the length of ligature material passes therebetween.

Jaws 24A and 24B are movable outwardly away from one another from the grasping position to an open, non-engaging, non-holding or non-grasping position by engagement of a distal end of actuator 18 with the jaws 24A and 24B when the actuator 18 is moved longitudinally relative to the engaging member 16 as explained further below. When moved to the open position, shown in FIGS. 11 and 12, the jaws 24A and 24B rotate or pivot about hinge segments 26A and 26B, respectively, in a direction away from the longitudinal axis of the engaging member 16. Accordingly, jaws 24A and 24B in the open position are disposed further away from one another and, therefore, are disposed further away from the engaging member longitudinal axis, than they are in the grasping position. In the open position, the distance between the forward edge segments 31A and 31B is greater than the distance between the forward edge segments 31A and 31B in the grasping position, and the distance between the forward edge segments 31A and 31B in the open position is large enough to permit passage therebetween of the ligature loops of ligature supply 14 as explained further below. The jaws can be designed in many various ways to be maintained in or biased toward the grasping position and to be movable to the open position. For example, jaws 24A and 24B can be made partly or entirely of resilient, flexible, or spring materials, such as materials having shape memory, for example, to flexibly, resiliently and/or spring bias the jaws toward the grasping position, to allow the jaws to pivot, rotate or deform from the grasping position to the open position in response to engagement with actuator 18 and to automatically return, move or restore the jaws to the grasping position in response to disengagement with actuator 18. In the case of engaging member 16, the jaws 24A and 24B are made entirely or substantially entirely of resilient, flexible or spring materials allowing the walls of the jaws to temporarily, non-permanently deform when the jaws are moved to the open position.

The actuator or deployer 18 comprises an elongate actuator plate 32 terminating proximally at a transverse or perpendicular end wall or flange 33 configured or provided with protruding flanges or ears 34 and terminating distally at a distal end defined by an arcuate or convex edge 35. The actuator 18 is disposed in the lumen or hollow interior of engaging member 16 such that a plane containing the actuator plate 32 is transverse or perpendicular to the forward edge segments 31A and 31B. As shown in FIG. 5, the plane containing the actuator plate 32 is offset from and not aligned with the longitudinal axis of engaging member 16 such that the actuator plate 32 is disposed in the engaging member lumen off-center or slightly to one side of the engaging member. The actuator plate 32 is of uniform minimal thickness and has a height such that lateral edges 36 of the actuator plate joined to arcuate edge 35 are in contact with the inner surface of the engaging member body 23 while allowing the engaging member 16 and the actuator 18 to move longitudinally relative to the engaging member 16. The actuator 18 has a length such that the lateral edges 36 are spaced proximally from the curved inner surfaces of the walls of jaws 24A and 24B when a hand grip 50 of handle 22 is in a rest position as explained further below whereby the jaws 24A and 24B remain in the grasping position as shown in FIG. 3. The arcuate edge 35 has a curvature corresponding to the curvature of the inner surfaces of the walls of the jaw members allowing the distal end of actuator 18 to fit within the rounded nose defined by the jaws 24A and 24B. Flanges or ears 34 are spaced 180° from one another and are laterally offset from the plane of the actuator plate to be longitudinally aligned with flanges 25 when the actuator 18 is disposed in the engaging member 16.

A plurality of retention members or fingers 38 are disposed on an inner face 39 of the actuator plate 32, the inner face 39 facing the middle or center of the lumen of the engaging member 16. Retention members 38 are longitudinally aligned with one another along the actuator plate 32 and are centrally disposed between lateral edges 36. Each retention member 38 has an attached end secured to the actuator plate 32 and a blunt or rounded free end opposite the attached end, with the retention member being curved or angled distally or forwardly from the actuator plate. The free end of each retention member 38 is spaced from the inner face 39 of the actuator plate to form a mouth communicating with a pocket or recess 40 defined between the retention member and the inner face 39 of the actuator plate. The pockets 40 are of a size to receive knotting elements of the ligature loops of ligature supply 14 and; as shown in FIG. 5, the pockets 40 are preferably aligned or substantially aligned with the longitudinal axis of the engaging member 16. A distal most retention member is disposed adjacent arcuate edge 35 with the mouth thereof aligned with edge 35. The pockets 40 are spaced longitudinally from one another a distance corresponding to the distance or spacing between the knotting elements of the ligature supply 14 as explained further below.

Knotting element pusher or mover 20, as shown in FIGS. 1–3, comprises a tubular or hollow elongate, cylindrical body 41 and a pusher end 42 joined to a forward or distal end of the pusher body at a circumferential or peripheral junction 43. The pusher body terminates proximally at an open proximal end mounted to a finger grip 44 of handle 22. A pair of longitudinally extending slots 45 are formed in the pusher body 41 at 180° spaced locations about a longitudinal axis of the knotting element pusher 20, the slots 45 extending distally from the proximal end of the pusher body to extend along a portion of the length of the pusher body. Slots 45 have a length to permit longitudinal movement of the knotting element pusher 20 distally and proximally relative to the engaging member 16 and to permit longitudinal movement of the actuator 18 relative to the engaging member 16 during use as explained below. The pusher body 41 preferably has an external diameter or cross-sectional size sufficiently small to be introduced at an internal operative site in the body through a relatively small size or narrow endoscopic portal or opening for use in endoscopic procedures wherein the endoscopic portal or opening establishes communication with the internal operative site from externally thereof without the need for a substantial incision. The pusher body 41, which can be cylindrical as shown or noncylindrical, preferably has an internal diameter or size to closely receive the engaging member 16 while being movable longitudinally, proximally and distally, relative to the engaging member 16 via a manual force applied with finger grip 44 as explained below. Pusher end 42 is hollow and has a cross-sectional configuration that tapers distally from junction 43 to a distal tip. Pusher end 42 has a conical configuration; however, various other configurations can be utilized for the pusher end. A distal portion of the knotting element pusher 20 is slit or cut to define a plurality of push fingers 46. For example, the distal portion of pusher 20 is slit or cut at 90° spaced locations about the longitudinal axis of the knotting element pusher 20, the slits or cuts 47 extending longitudinally along the pusher end 42 from the distal tip to junction 43 and extending longitudinally, proximally from junction 43 to continue part way along the pusher body 41. The slits 47 terminate proximally at rounded edges on the pusher body and define four push fingers 46 having distal tips 48, respectively, together defining the distal tip of the pusher end 42. It should be appreciated, however, that the distal portion of the knotting element pusher can be designed in various ways to include any desired number of push fingers.

The distal portion of the knotting element pusher 20 is disposed in a normal, contracted or closed position wherein distal tips 48 are disposed close to one another and close to the pusher longitudinal axis while being separated slightly from one another by a distance allowing passage of the length of filamentous ligature material 70 between the distal tips 48 while preventing passage of the knotting elements therebetween. The distal portion of the knotting element pusher 20 is movable from the contracted position to an expanded or open position wherein push fingers 46 are spread outwardly away from one another in a direction away from the longitudinal axis of the knotting element pusher 20. In the expanded position, distal tips 48 are disposed further away from one another and further away from the pusher longitudinal axis than they are in the contracted position to be separated from one another by a greater distance allowing the knotting elements and, therefore, the ligature loops of the ligature supply, to pass therebetween. The distal portion of the knotting element pusher can be designed in many ways to be normally disposed in the contracted position, to be movable to the expanded position and to be movable from the expanded position back to the contracted position. In the case of knotting element pusher 20, the distal portion thereof is made of resilient, flexible or spring materials, such as materials having shape memory, for example, such that the push fingers are resiliently, flexibly or spring biased to the contracted position. The push fingers 46 can be deformable to temporarily, non-permanently deform in the expanded position. It should be appreciated that the pusher 20 can be designed with various structure other than push fingers 46 to present a distal portion movable between contracted and expanded positions. The distal tips of the push fingers can be in contact with one another when no ligature material passes therebetween, in which case the tips 48 will be spaced from one another when the length of ligature material 70 passes therebetween in the contracted position.

Figure 6:
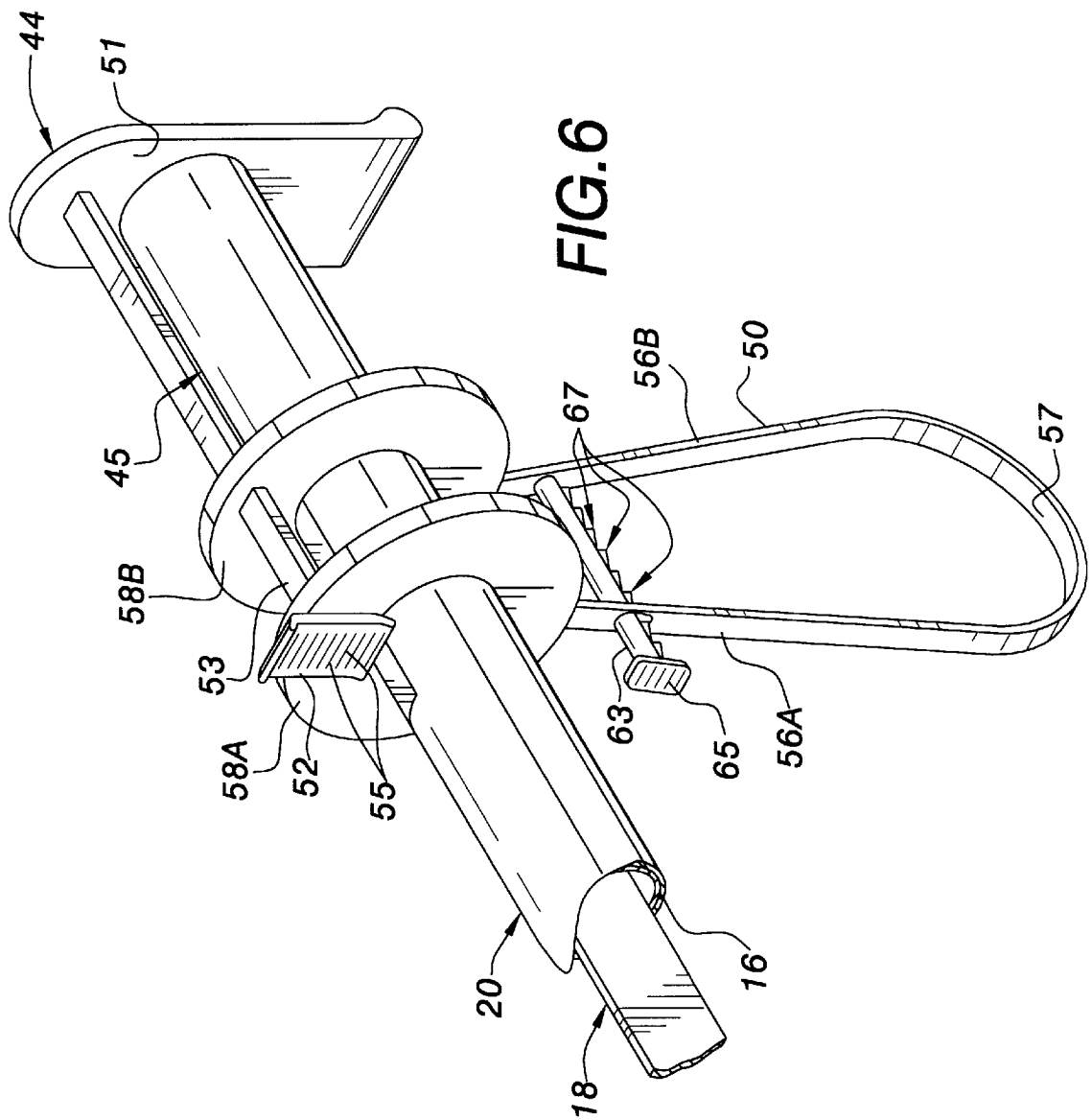
FIG. 6 is a broken perspective view of a proximal portion of the instrument body.

Handle 22 includes finger grip 44 and U-shaped hand grip 50. The finger grip 44 includes a proximal or rearward push button or knob 51 mounted to the proximal end of the pusher body 41 and a distal or forward push button or knob 52 coupled with the proximal push button 51 by an arm 53. Proximal push button 51 has a substantially planar, oblong configuration, and a cylindrical protrusion 54 extends perpendicularly, distally from the proximal push button. The protrusion 54 is received within the open proximal end of the pusher body 41 such that the proximal push button 51 is disposed perpendicular or transverse to the longitudinal axis of the knotting element pusher 20. The pusher 20 is attached to the finger grip 44 for movement therewith; and, in the case of instrument 10, protrusion 54 is adhesively attached to the pusher body 41. The proximal push button 51 has an arcuate upper edge and a straight, thickened lower edge that is flared in the proximal direction. Distal push button 52 has a substantially planar, square configuration with thickened upper and lower edges that are flared in the distal direction. Arm 53 includes an elongate strip of material extending between proximal push button 51 and distal push button 52, the arm 53 being spaced laterally from the pusher body 41 on a side thereof opposite hand grip 50. Arm 53 extends parallel to the longitudinal axis of the knotting element pusher 20 with the push buttons 51 and 52 parallel to one another. One or both of the push buttons 51 and 52 can be grooved, roughened or provided with ridges, for example, along finger contacting or finger engaging surfaces thereof. As shown in FIGS. 1 and 6, a distally facing, finger engaging surface of distal push button 52 is provided with horizontal ridges 55 to facilitate contact or gripping by a finger of the hand grasping hand grip 50. Similar ridges can be provided on the proximally facing surface of proximal push button 51 to facilitate engagement by the thumb of the hand grasping hand grip 50 as shown in FIG. 1.

Hand grip 50 includes a forward leg 56A and a rearward leg 56B having lower ends, respectively, connected to one another by a curved base 57. An upper end of leg 56A is connected to a flat or planar retention ring or flange 58A having recesses 59A therein receiving flanges 25 of engaging member 16. An upper end of leg 56B is connected to a retention ring 58B, similar to retention ring 58A, having recesses 59B therein receiving flanges 34 of actuator 18. The curved base 57 maintains the hand grip 50 in a rest position as shown in FIGS. 1 and 3 wherein legs 56A and 56B are spaced from and parallel to one another. In the rest position, hand grip 50 positions engaging member 16 and actuator 18 longitudinally relative to one another such that the actuator 18 is in a neutral longitudinal position wherein the lateral edges 36 of the actuator do not engage the curved inner walls of the jaws and the jaws, therefore, remain in the closed position. Hand grip 50 is entirely or partly made of resilient, flexible or spring materials, such as materials having shape memory, for example, allowing the hand grip 50 to be manually squeezed or compressed via legs 56A and 56B for movement from the rest position to a compressed or squeezed position wherein the upper ends of the legs are disposed closer to one another than they are in the rest position and allowing the hand grip to return automatically to the rest position when the manual squeezing or compressive force is removed. To facilitate squeezing operation of hand grip 50, the upper ends of legs 56A and 56B can be pivotally attached to the retention rings 58A and 58B, respectively, such as via pivot pins, hinges or joints.

The knotting element pusher 20 slidably passes through longitudinally aligned openings 60A and 60B in the retention rings 58A and 58B, respectively, with the flanges 25 of the engaging member and the flanges 34 of the actuator slidably disposed in the slots 45 of the pusher body 41 and the arm 53 slidably passing through apertures 61A and 61B in the retention rings, respectively. A helical coil spring 62 is disposed in the pusher body and is mounted in compression between the end wall 33 of the actuator 18 and the protrusion 54 of finger grip 44 to bias the knotting element pusher 20 longitudinally to an initial longitudinal position as shown in FIGS. 1 and 3 wherein the distal tips 48 are disposed distally of jaws 24A and 24B with the distal portion of the pusher 20 in the contracted position and the actuator in the neutral position. In the initial position, the proximal push button 51 is proximally spaced from rearward leg 56B and retention ring 58B, and the distal push button 52 is distally spaced from forward leg 56A and retention ring 58A.

Hand grip 50 includes a locking mechanism for locking the hand grip in a compressed or squeezed position and comprises an elongate locking bar 63 having a first end rotatably mounted to leg 56B at a joint or pivot 64 and a second, free end formed or provided with an operating knob 65. The locking bar 63 passes through an aperture 66 in leg 56A such that the knob 65 is disposed distally of leg 56A. The locking bar 63 has a circular cross-sectional configuration between the first and second ends, and a plurality of protruding locking teeth 67, longitudinally aligned with one another, extend along the locking bar between the first and second ends thereof. As shown in FIG. 7, each tooth 67 includes a proximal locking surface 68 perpendicular or transverse to the locking bar 63 and a distal ramp surface 69 joined to the locking bar at a base, the ramp surface being angled away from the locking bar to meet the locking surface at a crest. Each locking surface 68 is spaced from the base of a next proximal tooth a distance D at least as great as the thickness of leg 56A. Locking bar 63 is mounted by joint 64 to extend perpendicularly to legs 56A and 56B with a longitudinal axis of the locking bar 63 laterally offset from or not aligned with the center of aperture 66 such that the locking bar is disposed to one side of aperture 66. Locking bar 63 is rotatably or pivotally mounted to leg 56B by joint 64 such that the locking bar is rotatable about its longitudinal axis. The locking bar 63 is normally disposed in a first rotational or unlocked position shown in FIGS. 6 and 7 wherein a side of the locking bar opposite teeth 67 is in contact with an internal surface of aperture 66 and wherein locking surfaces 68 of teeth 67 are longitudinally aligned with aperture 66 to allow the locking bar to move or pass therethrough when the hand grip 50 is compressed or squeezed as shown in FIG. 6. The locking bar 63 is movable to a second rotational or locked position wherein the locking bar is rotated 180° about its longitudinal axis. In the second rotational position, the locking surfaces 68 of teeth 67 are no longer longitudinally aligned with aperture 66 but, rather, are longitudinally aligned with a solid, external distal surface of leg 56A as shown in FIG. 8. Accordingly, when the leg 56A is disposed between adjacent distal and proximal teeth 67, the locking surface 68 of the distal tooth will be in abutment with the external distal surface of leg 56A to prevent the hand grip from returning to the rest position after being squeezed or compressed , and the side of the locking bar between the adjacent distal and proximal teeth will be in contact with the internal surface of aperture 66. The locking bar 63 is rotatable about its longitudinal axis from the second rotational position to the first rotational position to unlock hand grip 50 for return automatically to the rest position. It should be appreciated that the locking bar can be flexibly, resiliently or spring biased into contact with the internal surface of aperture 66 to allow the locking bar to deflect to permit squeezing operation of the hand grip when the locking bar is in the second rotational position with the locking surfaces springing into engagement with the external distal surface of leg 56A in the manner of a ratchet.

As shown in FIG. 3, ligature supply 14 comprises the length of filamentous or thread-like ligature material 70 configured to form a plurality of interconnected, pre-formed, variable size or contractible ligature loops 72. Each ligature loop 72 includes a loop segment 73 of the length of ligature material and a knotting element 74 movable along the ligature material in a direction to contract or reduce the size of the loop segment 73 around anatomical structure to form a ligature. Movable knotting elements 74 are in the nature of slidable knots 74 formed from the length of ligature material 70. Ligature loops 72 are disposed at spaced locations along the length of ligature material such that connecting segments 75 of the length of ligature material extend between adjacent ligature loops. Knots 74 are of a size preventing passage of the knots 74 and, therefore, the ligature loops 72, between the forward edge segments 31A and 31B when the jaws 24A and 24B are in the grasping position and permitting passage of the knots 74 and, therefore, the ligature loops 72, between the forward edge segments when the jaws are in the open position. Knots 72 are of a size preventing passage of the knots 74 and, therefore, the ligature loops 72, between distal tips 48 when the distal portion of the knotting element pusher 20 is in the contracted position and permitting passage of the knots 74 and, therefore, the ligature loops, between the distal tips when the distal portion of the knotting element pusher is in the expanded position. The length of ligature material 70 comprises a filament having an external diameter or cross-sectional size permitting passage of the filament between forward edge segments 31A and 31B when the jaws 24A and 24B are in the grasping position and permitting passage of the filament between distal tips 48 when the distal portion of the knotting element pusher 20 is in the contracted position. With the exception of the distal most and the proximal most ligature loops, two connecting segments 75 extend from each knot 74, one connecting segment extending to the knot of a next distal ligature loop and the other connecting segment extending to the knot of a next proximal ligature loop. The knot of the distal most ligature loop 72' has one connecting segment 75' extending from the knot 74' thereof to the knot 74" of the next proximal ligature loop 72". The knot of the proximal most ligature loop has a connecting segment extending therefrom to the knot of the next distal ligature loop and a segment extending therefrom forming a tail for being grasped by jaws 24A and 24B when the loop segment of the proximal most ligature loop is contracted around anatomical structure to form a ligature. The number of ligature loops 72 is selected in accordance with the number of ligatures to be formed for a particular procedure such that all of the ligatures for a particular procedure can be formed without withdrawing the instrument 10 from the operative site. Knots 74 can be in the nature of slip, sliding or hangman's knots, for example, or any other type of knot permitting movement of the knot along the length of ligature material in the direction of the corresponding loop segment to contract or reduce the size of the corresponding loop segment. Applicant's prior application Ser. No. 08/533,504 incorporated herein by reference discloses one manner of forming knots and loop segments in a length of ligature material for use as a ligature supply in the present invention.

The ligature supply 14 is disposed in the lumen or hollow interior of the engaging member 16 with the knots 74 releasably retained, held, captured or engaged by retention members 38, respectively. Accordingly, the connecting segments 75 preferably have a length corresponding to the longitudinal spacing of the retention members 38. The ligature supply 14 is arranged in engaging member 16 with ligature loops 72 extending proximally from the corresponding retention members to facilitate deployment of the ligature loops externally of the instrument body. The ligature loops 72 are supported by the wall of the engaging member body 23; and, with the ligature loops so supported, the knots 74 are longitudinally aligned with the mouths of the retention members. Accordingly, the ligature supply is carried or advanced distally relative to the engaging member 16 when the actuator 18 is moved longitudinally, distally from the neutral position as explained below. The ligature supply is able to deflect laterally within the engaging member to allow the retention members 38 to move proximally past the knots after the ligature supply has been advanced by the actuator 18; and, after deflecting to allow proximal movement of the retention members therepast, the knotting elements return to a position of alignment with the mouths of the retention members as explained below. Protrusions such as hooks or ledges can extend from the inner face 39 of the actuator plate 72 to hold and/or support the connecting segments to maintain alignment of the knotting elements with the mouths of the retention members while allowing temporary lateral deflection of the ligature supply. The retention members 38 can have various configurations or shapes to releasably capture or hold the knotting elements for movement of the ligature loops distally with the actuator 18.

It should be appreciated that various other types of knotting elements capable of being moved along the ligature material to contract the loop segments, including separate knotting elements not formed from the length of ligature material, can be utilized in the present invention. It should be further appreciated that the knotting elements can be designed to prevent expansion of the loop segments once the loop segments have been contracted or reduced in size. Various knotting elements suitable for use in the present invention are disclosed in applicant's prior applications Ser. No. 08/533,504, Ser. No. 08/531,153, Ser. No. 08/366,285, Ser. No. 08/377,723 and Ser. No. 08/401,002, the disclosures of which are incorporated herein by reference.

Prior to use, ligating instrument 10 will be in the condition shown in FIGS. 1 and 3 with the knotting element pusher 20 disposed in the initial longitudinal position and the actuator 18 disposed in the neutral longitudinal position. Accordingly, jaws 24A and 24B will be disposed in the grasping position and the distal portion of the pusher 20 will be disposed in the contracted position with distal tips 48 disposed distally of jaws 24A and 24B. Finger grip 44 is biased relative to hand grip 50 by spring 62 to position the pusher 20 in the initial position with proximal push button 51 spaced proximally from retaining ring 58B and distal push button 52 spaced distally from retaining ring 58A. Hand grip 50 will be disposed in the rest position to maintain the neutral position for actuator 18. Accordingly, prior to use, the distal end of actuator 18 will be disposed within jaws 24A and 24B in the grasping position, and the jaws in the grasping position will be disposed within the pusher 20 with the distal portion of the pusher in the contracted position. The distal most ligature loop 72' can be disposed externally of the instrument body 12 with the knot 74' thereof disposed distally of pusher distal tips 48 and with the remaining ligature loops disposed within engaging member 16. The connecting segment 75' extending from knot 74' to the knot 74" of the next proximal ligature loop 72" passes between tips 48 and forward edge segments 31A and 31B. The connecting segment 75' is held between the forward edge segments, and the knots of the remaining ligature loops are releasably held, captured, engaged or retained by retention members 38, respectively, with the knot 74" held by the distal most retention member. Accordingly, the remaining ligature loops are longitudinally spaced from one another in series along the actuator 18 with the knots thereof received in pockets 40 of retention members 38 and with connecting segments 75 thereof extending between adjacent retention members.

It should be appreciated that no ligature loop need be disposed externally of the instrument body 12 prior to introduction of a distal end of the instrument body at an internal operative site and such may be desirable to facilitate positioning the distal end of the instrument body at the operative site through a relatively small size or narrow portal without snagging or catching. Accordingly, ligature loop 72' can be disposed in the instrument body 12 with the knot 74' thereof held by the distal most retention member, in which case the ligature loop 72' can be deployed externally of the instrument body prior to or subsequent to introduction of the distal end of the instrument body at an internal operative site. The ligature loop 72' is deployed externally of the instrument body 12 in the same manner as described below for external deployment of ligature loop 72" and the other ligature loops. Where the ligature loop 72' is disposed within the engaging member 16 prior to use, the ligature loop 72' can be provided with a tail extending from knot 74' between jaws 24A and 24B and between pusher tips 48 to terminate externally of the instrument body 12 allowing the tail to be grasped externally of the instrument body with a separate instrument, if desired, to facilitate external deployment of ligature loop 72'.

When it is desired to form one or more ligatures in anatomical structure, including anatomical tissue, tubular anatomical structure and organ structure, for example, at an operative site in a body, the distal end of the instrument body 12 defined by pusher end 42 is introduced at the operative site. In endoscopic operative procedures, the pusher end 42 is typically introduced at an internal operative site through a relatively small size or narrow channel or portal including naturally or artificially formed anatomical openings or passages or structure such as a portal sleeve or cannula establishing communication with the internal operative site from externally thereof. The pusher end 42 is introduced and positioned at the internal operative site via manipulation of the instrument body 12 by a hand grasping hand grip 50. The distal end of the instrument body is introduced at the operative site with pusher 20 in the initial position and hand grip 50 in the rest position with actuator 18 in the neutral position.

Once the distal end of the instrument body 12 has been introduced at the internal operative site with handle 22 held externally of the operative site which, in endoscopic procedures, typically entails holding the handle externally of the body, the externally deployed ligature loop 72' is positioned around the anatomical structure S to be ligated as shown in FIG. 3. Where ligature loop 72' is not externally deployed when the distal end of the instrument body is introduced at the operative site, the ligature loop 72' is deployed externally of the instrument body in the manner described below after the distal end of the instrument body has been introduced at the operative site, and thereafter the externally deployed loop 72' is positioned around the anatomical structure to be ligated.

Figure 9:
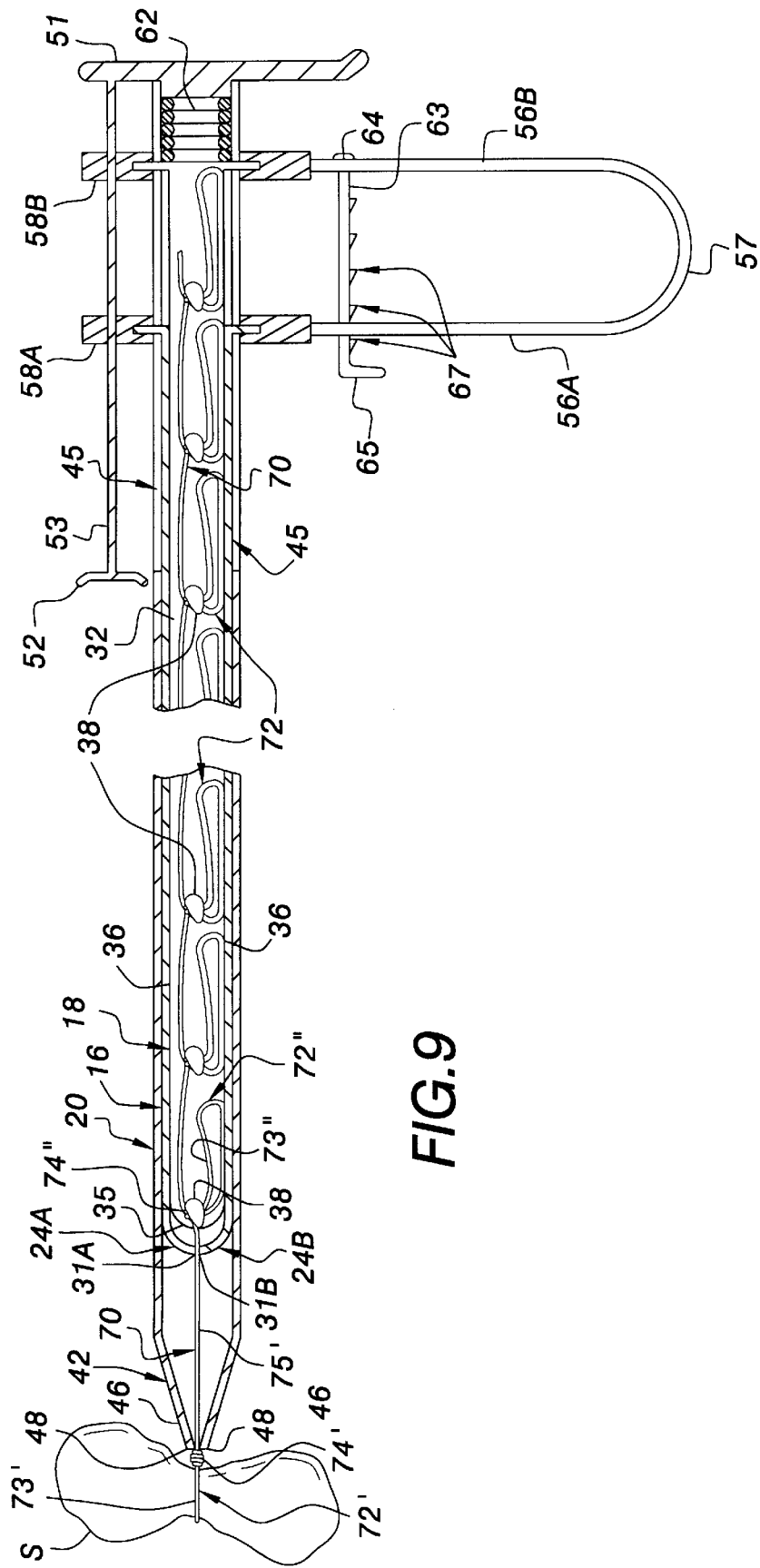
FIG. 9 is a broken, side sectional view of the ligating instrument showing the externally deployed ligature loop contracted around the anatomical structure to form a ligature.

In order to contract the loop 72' around the anatomical structure S to form a ligature, the surgeon grasps handle 22 as shown in FIG. 1 with the thumb of one hand adjacent the proximal push button 51 and the remaining fingers of the one hand disposed between legs 56A and 56B. Utilizing the thumb of the one hand, the surgeon depresses or moves the proximal push button 51 distally toward retaining ring 58B causing the knotting element pusher 20 to be moved longitudinally, distally relative to the engaging member 16 against the bias of spring 62 from the initial longitudinal position to an extended longitudinal position, as permitted by slots 45 in the pusher body 41. The hand grip 50 remains in the rest position such that the engaging member 16 and the actuator 18 do not move relative to one another. Distal movement of the knotting element pusher 20 from the initial position causes the distal tips 48 of the push fingers 46 to move the knot 74' of the ligature loop 72' distally, i.e. in the direction of loop segment 73', along the length of ligature material 70 as shown in FIG. 9. Movement of the knotting element 74' in the direction of the loop segment 73' of ligature loop 72' causes the loop segment 73' to be contracted or reduced in size around the anatomical structure S to form a ligature.

The manual force applied by the surgeon to the proximal push button 51 to move the pusher 20 distally from the initial position can be controlled to obtain a desired tension or tightness for the contracted loop segment 73', and the surgeon can tactilely sense or feel contraction of the loop segment for controlled tensioning. As the knotting element pusher 20 is moved distally to contract the loop segment 73', the connecting segment 75' is held between the forward edge segments 31A and 31B of the jaws 24A and 24B, respectively, to facilitate movement of knot 74' along the length of ligature material 70 and contraction of the loop segment 73'. If desired, the engaging member 16 can be backed away from the structure S via the hand grip 50 so that the connecting segment 75' remains taut.

Figure 10:
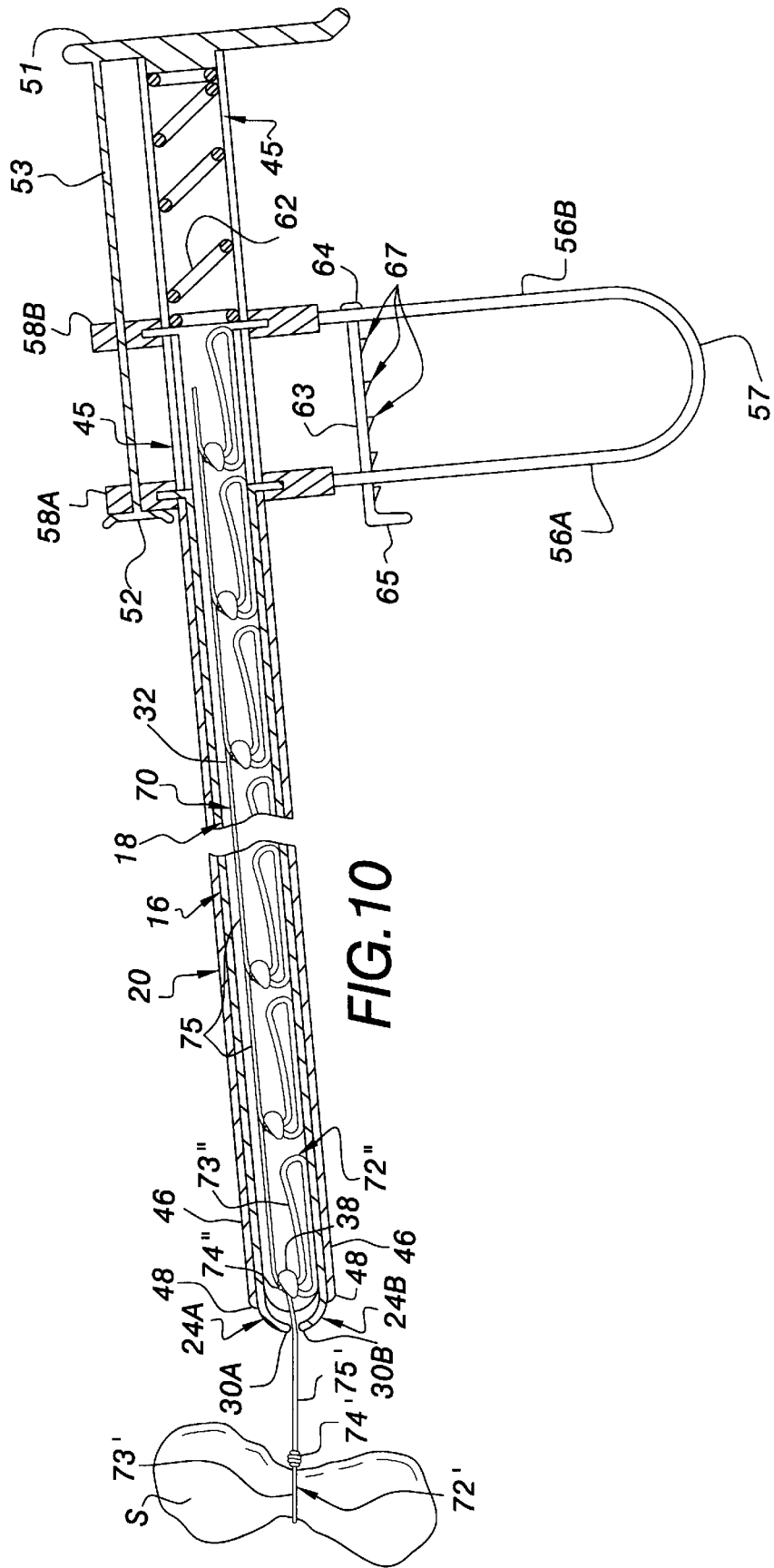
FIG. 10 is a broken, side sectional view of the ligating instrument showing the ligature material cut proximally of the ligature to sever the ligature from the remainder of the ligature supply.

Once the ligature has been formed with desired tension around the anatomical structure S, the thumb is removed from the proximal push button 51 causing the pusher 20 to return to the initial position due to the bias of spring 62. The index finger of the hand grasping handle 22 is utilized to engage distal push button 52 and to depress or move the push button 52 proximally toward retaining ring 58A as shown in FIGS. 6 and 10. As shown in FIG. 10, movement of distal push button 52 proximally causes the knotting element pusher 20 to move longitudinally, proximally relative to the engaging member 16 and the actuator 18 from the initial longitudinal position to a retracted longitudinal position. The engaging member 16 and the actuator 18 do not move relative to one another since the hand grip 50 is not squeezed and thusly remains in the rest position. The distal push button 52 is moved proximally until it is in abutment with the retaining ring 58A, which serves as a positive stop for the pusher 20 in the retracted position. Movement of pusher 20 to the retracted position causes the pusher end 42 to flex or deform due to engagement of the inner surfaces of push fingers 46 with the jaws 24A and 24B. Accordingly, the push fingers 46 will be moved from the contracted position to the expanded position, and the jaws 24A and 24B will protrude distally beyond the distal tips 48 of the push fingers as shown in FIG. 10. Accordingly, the sharpened intermediate edge segments 30A of jaw 24A will be exposed at the distal end of the instrument body 12. The instrument body 12 is pivoted, rotated, angled or tilted laterally via manipulation with hand grip 50, causing the connecting segment 75' to be moved laterally between the jaws 24A and 24B to contact one of the intermediate edge segments 30A to be cut or severed thereby as shown in FIG. 10. Accordingly, the ligature material 70 is cut away from or proximally of the knot 74' of the ligature thusly severing the ligature from the remainder of the ligature supply 14.

Figure 11:
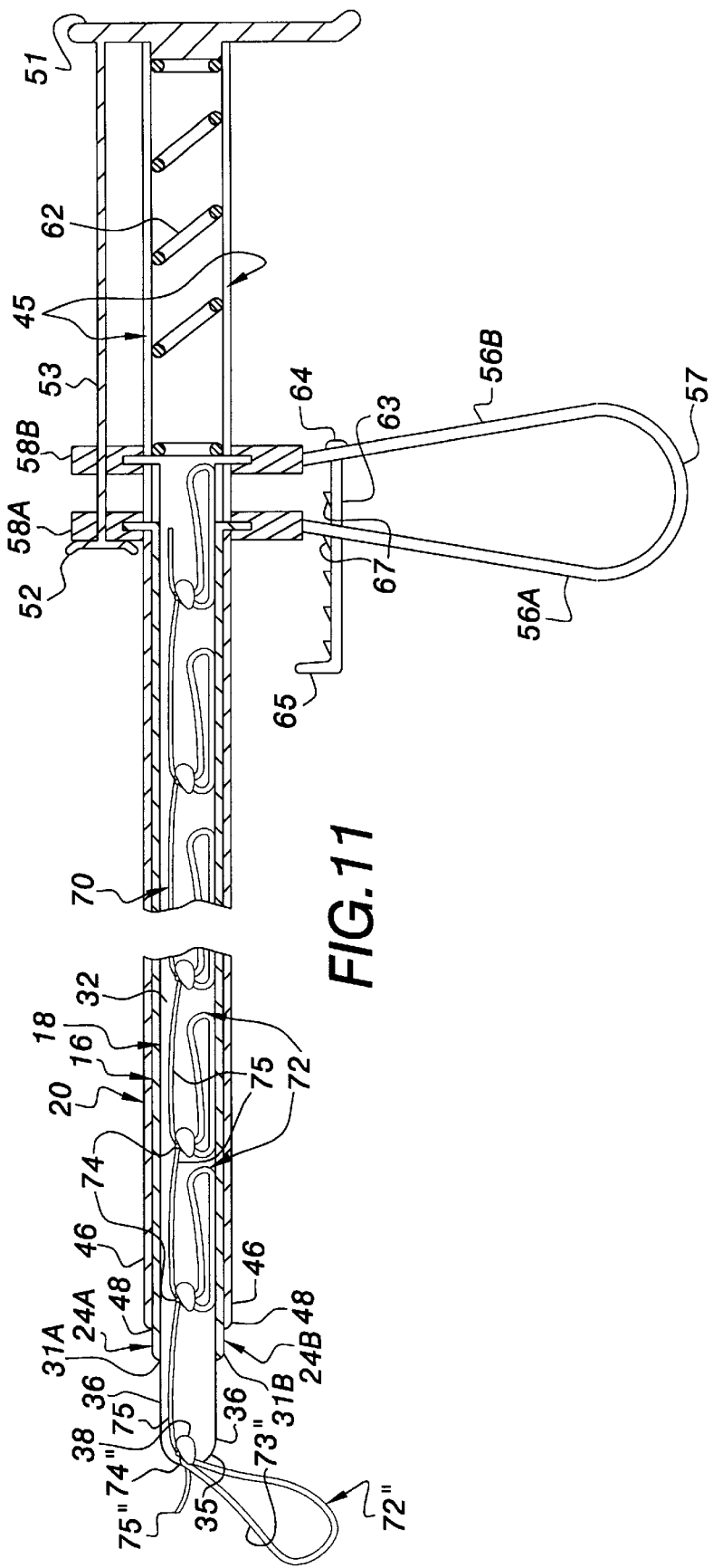
FIG. 11 is a broken, side sectional view of the ligating instrument showing the next proximal ligature loop of the ligature supply advanced distally by the deployer.

In order to deploy the next ligature loop 72" externally of the instrument body, the distal push button 52 is held against the retaining ring 58A to maintain the pusher 20 in the retracted position, and the hand grip 50 is manually squeezed or compressed causing rearward leg 56B to be moved toward forward leg 56A to move actuator 18 longitudinally, distally relative to the engaging member 16 from the neutral longitudinal position to an extended or deployed longitudinal position as shown in FIGS. 11 and 12. Distal movement of actuator 18 from the neutral position relative to engaging member 16 causes the lateral edges 36 of the actuator to engage the inner surfaces of the curved walls of the jaws 24A and 24B, respectively, such that the jaws 24A and 24B are moved from the grasping position to the open or non-grasping position. The actuator 18, which is moved distally relative to the pusher 20 since the pusher 20 is held in the retracted position, is moved far enough distally to pass through jaws 24A and 24B, and the ligature supply 14 is carried or advanced distally with the actuator. Accordingly, distal most retention member 38 and the ligature loop 72" held thereby are positioned externally of the jaws 24A and 24B. As shown in FIG. 12, the distal portion of pusher 20 and the jaws 24A and 24B temporarily deform in the expanded and open positions, respectively. The locking bar 63 can be rotated from the first rotational position to the second rotational position wherein a locking surface 68 of one of the teeth 67 engages the external distal surface of the forward leg 56A to lock the hand grip 50 in the compressed or squeezed position. The loop segment 73" of the now externally deployed ligature loop 72" can be positioned around the same or another anatomical structure to be ligated with the handgrip 50 locked in the squeezed position and, therefore, the actuator 18 locked in the extended position, by locking bar 63, or the actuator 18 can be returned to the neutral position prior to placing the loop segment 73" around anatomical structure to be ligated. In order to return the actuator 18 to the neutral position, the compressive or squeezing force on legs 56A and 56B is removed allowing the hand grip 50 to return automatically to the rest position due to the bias of base 57. Where the hand grip 50 has previously been locked in the squeezed or compressed position, the hand grip must first be unlocked in order to permit return to the rest position. The hand grip 50 is unlocked by rotating the locking bar 63 from the second rotational position to the first rotational position allowing the hand grip to return automatically to the rest position when the compressive force thereon is removed.

Return of the hand grip 50 to the rest position causes the actuator 18 to move longitudinally, proximally relative to the engaging member 16 from the extended position to the neutral position. When the actuator 18 moves proximally from the extended position to the neutral position, the ligature supply 14 remains in the advanced position such that the actuator 18 moves proximally relative to the ligature supply. Accordingly, each knotting element 72 is released, disengaged or freed from the retention member that held it. Movement of the actuator 18 from the extended position to the neutral position causes the jaws 24A and 24B to return automatically to the grasping position, and the ligature loop 72" will be disposed externally of the jaws. The connecting segment 75" between the knot 74" of the externally deployed ligature loop 72" and the knot of the next proximal ligature loop disposed within the engaging member 16 passes between the forward edge segments 31A and 31B and is held thereby. Once the actuator 18 has returned to the neutral position, each retention member will not only have released the knotting element it previously held but will have moved proximally past the knotting element next proximal to the knotting element it previously held, as permitted by lateral deflection of the ligature supply, and will releasably engage or hold the next proximal knotting element, with the exception of the proximal most retention member which does not engage a knotting element since the proximal most knotting element has moved up to the next distal retention member. For example, the distal most retention member, which previously held knot 74", now holds the knot of the ligature loop next proximal to ligature loop 72".

Once the actuator 18 has returned to the neutral position, the proximal force on distal push button 52 is removed; and, upon release of push button 52, the knotting element pusher 20 will automatically return to the initial position with the distal portion thereof in the contracted position and the distal tips 48 of the push fingers 46 disposed proximally of the knot 74" as shown in dotted lines in FIG. 12. The ligating instrument 10 is now ready for use to form another ligature without withdrawal of the ligating instrument from the operative site.

It should be appreciated that a separate instrument, such as a grasper or forceps, can be utilized to grasp the ligature material to pull the ligature supply distally through the instrument body to deploy or assist in deploying one or more ligature loops. The frictional holding force of the jaws 24A and 24B on the length of ligature material can be selected to allow the ligature supply to be pulled distally through the instrument body and/or to allow the instrument body to be backed up or moved proximally relative to the ligature supply when the ligature material is held externally of the instrument body. It should also be appreciated that more than one ligature loop can be disposed externally of the instrument body for forming a double loop ligature as disclosed in applicant's prior application Ser. No. 08/533,504 incorporated herein by reference; and, accordingly, each ligature loop can comprise two loop segments.

FIG. 13 illustrates at 116 a modification of an engaging member for use in a ligating instrument according to the present invention. Engaging member 116 is similar to engaging member 16 except that the forward edge segments 131A and 131B for engaging member 116 include teeth or ridges 137 extending therealong to enhance gripping of the ligature material 170 between the jaws 124A and 124B.

Another modification of an engaging member for use in a ligating instrument according to the present invention is illustrated at 216 in FIG. 14. Engaging member 216 is similar to engaging member 16 except that the forward edge segment 231A of jaw 224A of engaging member 216 is spaced distally from the forward edge segment 231B of jaw 224B of engaging member 216. The forward edge segment 231B is disposed slightly within jaw 224A, and there is a space between the forward edge segments 231A and 231B communicating with the hollow interior of the jaws. A connecting segment 275 of the length of ligature material 270 extends from a knot 274 of ligature loop 272 held by a distal most retention member 238 of actuator 218 and passes through the space between the forward edge segments 231A and 231B to form a tail terminating externally of the instrument body. Accordingly, engaging member 216 is illustrative of an engaging member wherein the forward edge segments are not in alignment with one another in that one of the forward edge segments is disposed distally of the other forward edge segment in overlapping relation. Tail 275 can be grasped with a separate instrument externally of the jaws, and the tail can be pulled distally to deploy or assist in deploying the ligature loop 272.

The instrument body of the ligating instrument can be made of any desirable medical grade materials to be reusable or to be disposable for single patient use. The distal end of the engaging member can be designed in many ways and with various configurations providing movement between the closed or grasping position and the open or non-grasping position. The distal end of the engaging member can have any desirable configuration to engage the ligature material passing therethrough and the holding force of the engaging member distal end on the ligature material can be selected in accordance with procedural use. Where jaws are utilized as the engaging member distal end, the jaws can be formed integrally, unitarily with the body of the engaging member or separately therefrom. The cutting edges can have various configurations or locations in accordance with the structure or design of the engaging member distal end; and, where jaws are utilized, the cutting edges can be provided on either one or both of the jaws. Cutting of the length of ligature material to sever a ligature from the remainder of the ligature supply can also be accomplished with the use of a separate cutting instrument introduced at the operative site. The instrument body can include various handles, and the hand grip can include a pistol grip structure as well as various pivotable hand grips. Various hand grips suitable for use in the present invention are disclosed in the prior applications incorporated herein by reference. Where the hand grips include movable or pivotable legs, each leg can be movable or pivotable relative to the other leg, or one of the legs can be movable or pivotable while the other leg remains stationary or fixed. The ligating instrument can be designed to obtain the extended position for the actuator and/or the open position for the engaging member distal end via movement of the actuator alone relative to the engaging member, movement of the engaging member alone relative to the actuator or movement of both the actuator and the engaging member relative to one another. The distal portion of the knotting element pusher can have various configurations allowing movement between contracted and expanded positions. The finger grip can have various structural configurations for operation of the knotting element pusher by the hand grasping the hand grip including rotatable knobs or collars for moving the pusher longitudinally in response to rotation of the knobs or collars. The ligature supply can be arranged in the instrument body in many various ways, and the actuator can have various structure to facilitate advancement of the ligature supply and deployment of the ligature loops externally of the instrument body. Where more than one ligature loop is positioned around anatomical structure, the ligature loops can be tightened together or sequentially one at a time. The ligating instrument according to the present invention is usable in single puncture or multiple puncture endoscopic operative procedures, and the various instruments utilized in the ligating procedure can be introduced at the internal operative site through the same or different endoscopic portals.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A ligating instrument for forming ligatures in anatomical structure at an internal operative site in a body comprising an elongate knotting element pusher having a distal end for being introduced at the operative site, a proximal end and a lumen between said distal and proximal ends;

a ligature supply disposed in said lumen and including a continuous length of filamentous ligature material forming a plurality of preformed, contractible, closed ligature loops and connecting segments extending between said ligature loops, said connecting segments structurally connecting said ligature loops to one another in series, each of said ligature loops having a knotting element movable along said ligature material in a direction to contract said ligature loop around anatomical structure; and a deployer disposed in said lumen for selectively deploying one of said ligature loops externally of said distal end, said pusher being movable along said ligature material to move said knotting element of said externally deployed ligature loop in said direction to contract said externally deployed ligature loop around anatomical structure to form a ligature.

2. A ligating instrument as recited in claim 1 and further including an engaging member disposed in said lumen for holding said connecting segment of said externally deployed ligature loop as said pusher moves said knotting element of said externally deployed ligature loop to contract said externally deployed ligature loop around the anatomical structure.

3. A ligating instrument as recited in claim 2 wherein said distal end of said pusher is movable from a contracted position wherein said connecting segments can pass therethrough but said ligature loops cannot pass therethrough to an expanded position wherein said ligature loops can pass therethrough and said pusher is movable longitudinally relative to said engaging member to move said distal end from said contracted position to said expanded position to permit external deployment of one of said ligature loops and from said expanded position back to said contracted position.

4. A ligating instrument as recited in claim 3 wherein said pusher has an initial longitudinal position relative to said engaging member wherein said distal end is in said contracted position, said pusher being movable longitudinally, proximally relative to said engaging member from said initial position to move said distal end to said expanded position and being movable longitudinally, distally relative to said engaging member from said initial position with said distal end in said contracted position to move said knotting element of said externally deployed ligature loop in said direction to contract said externally deployed ligature loop around the anatomical structure.

5. A ligating instrument as recited in claim 4 wherein said distal end of said pusher includes a plurality of push fingers biased inwardly toward one another in said contracted position and spread outwardly away from one another in said expanded position, said push fingers having distal tips for engaging said knotting element of said externally deployed ligature loop when said pusher is moved longitudinally, distally from said initial position with said distal end in said contracted position.

6. A ligating instrument for forming ligatures in anatomical structure at an internal operative site in a body comprising an elongate knotting element pusher having a distal end for being introduced at the operative site, a proximal end and a lumen between said distal and proximal ends;

a ligature supply disposed in said lumen and including a plurality of preformed, contractible ligature loops of filamentous ligature material and connecting segments of said ligature material extending between said ligature loops, each of said ligature loops having a knotting element movable along said ligature material in a direction to contract said ligature loop around anatomical structure;

a deployer disposed in said lumen for selectively deploying one of said ligature loops externally of said distal end, said pusher being movable along said ligature material to move said knotting element of said externally deployed ligature loop in said direction to contract said externally deployed ligature loop around anatomical structure to form a ligature; and an engaging member disposed in said lumen for holding said connecting segment of said externally deployed ligature loop as said pusher moves said knotting element of said externally deployed ligature loop to contract said externally deployed ligature loop around the anatomical structure, said distal end of said pusher being movable from a contracted position wherein said connecting segments can pass therethrough but said ligature loops cannot pass therethrough to an expanded position wherein said ligature loops can pass therethrough and said pusher is movable longitudinally relative to said engaging member to move said distal end from said contracted position to said expanded position to permit external deployment of one of said ligature loops and from said expanded position back to said contracted position, said pusher having an initial longitudinal position relative to said engaging member wherein said distal end is in said contracted position, said pusher being movable longitudinally, proximally relative to said engaging member from said initial position to move said distal end to said expanded position and being movable longitudinally, distally relative to said engaging member from said initial position with said distal end in said contracted position to move said knotting element of said externally deployed ligature loop in said direction to contract said externally deployed ligature loop around the anatomical structure, said distal end of said pusher including a plurality of push fingers biased inwardly toward one another in said contracted position and spread outwardly away from one another in said expanded position, said push fingers having distal tips for engaging said knotting element of said externally deployed ligature loop when said pusher is moved longitudinally, distally from said initial position with said distal end in said contracted position, said engaging member including an elongate hollow body and a pair of jaws at a distal end of said hollow body, said ligature supply being disposed in said engaging member, said jaws being movable from a holding position wherein said connecting segments can pass between said jaws but said ligature loops cannot pass between said jaws and a non-holding position wherein said ligature loops can pass between said jaws, said deployer being disposed within said engaging member and being longitudinally movable relative to said engaging member to move said jaws from said holding position to said non-holding position to permit external deployment of one of said ligature loops when said distal end of said pusher is in said expanded position, said connecting segment of said externally deployed ligature loop being held between said jaws when said one ligature loop is externally deployed, said jaws being movable from said non-holding position to said holding position to release said connecting segment of said externally deployed ligature loop.

7. A ligating instrument as recited in claim 6 wherein said deployer is movable longitudinally, distally relative to said engaging member from a neutral position to a deployed position and is movable longitudinally, proximally relative to said engaging member from said deployed position back to said neutral position, said jaws are biased inwardly toward one another in said holding position and said deployer moves said jaws outwardly away from one another to said non-holding position when said deployer is moved from said neutral position to said deployed position, said jaws returning to said non-holding position when said deployer is moved from said deployed position back to said neutral position, said deployer having a distal end disposed within said jaws in said neutral position and disposed externally of said jaws in said extended position.

8. A ligating instrument as recited in claim 7 wherein said deployer is movable to said deployed position when said pusher is in said expanded position and said distal end of said deployer is disposed externally of said distal end of said pusher when said deployer is in said deployed position.

9. A ligating instrument as recited in claim 8 wherein at least one of said jaws includes a cutting edge for cutting said connecting segment of said externally deployed ligature loop after a ligature has been formed with said externally deployed ligature loop to sever the ligature from the remainder of said ligature supply.

10. A ligating instrument as recited in claim 9 wherein said jaws include opposed grasping edges having teeth for frictionally holding said connecting segments.

11. A ligating instrument for forming ligatures in anatomical structure at an internal operative site in a body comprising
an instrument body having a distal end for being introduced at the operative site, a proximal end for being disposed externally of the operative site and a lumen between said distal and proximal ends; and
a ligature supply disposed in said lumen including a plurality of preformed, contractible ligature loops formed of a continuous length of filamentous ligature material, said ligature loops having knotting elements movable along said ligature material in a direction to contract said ligature loops around anatomical structure to form ligatures, said instrument body including a deployer for sequentially deploying said ligature loops externally of said instrument body, an operating member for moving said knotting elements of the externally deployed ligature loops in said direction to contract the externally deployed ligature loops around anatomical structure to form ligatures and a handle at said proximal end for operating said deployer and said operating member.

12. A ligating instrument as recited in claim 11 wherein said handle includes a hand grip for operating said deployer and a finger grip for operating said operating member independently of said deployer.

13. A ligating instrument as recited in claim 12 wherein said operating member includes an elongate, hollow knotting element pusher having a longitudinal axis and a plurality of push fingers disposed around said axis, said knotting element pusher having an initial longitudinal position wherein said push fingers are disposed in a contracted position proximally of a knotting element of an externally deployed ligature loop, said push fingers in said contracted position being disposed close to said axis for engaging said knotting element of the externally deployed ligature loop, said knotting element pusher being movable longitudinally, distally from said initial position to an extended longitudinal position with said push fingers in said contracted position to move said knotting element of the externally deployed ligature loop in said direction to contract the externally deployed ligature loop to form a ligature.

14. A ligating instrument as recited in claim 13 wherein said instrument body further includes an engaging member for holding said ligature material as said knotting element of the externally deployed ligature loop is moved by said knotting element pusher in said direction.

15. A ligating instrument for forming ligatures in anatomical structure at an internal operative site in a body comprising
an instrument body having a distal end for being introduced at the operative site, a proximal end for being disposed externally of the operative site and a lumen between said distal and proximal ends; and
a ligature supply disposed in said lumen including a plurality of preformed, contractible ligature loops of filamentous ligature material, said ligature loops having knotting elements movable along said ligature material in a direction to contract said ligature loops around anatomical structure to form ligatures, said instrument body including a deployer for sequentially deploying said ligature loops externally of said instrument body, an operating member for moving said knotting elements of the externally deployed ligature loops in said direction to contract the externally deployed ligature loops around anatomical structure to form ligatures and a handle at said proximal end for operating said deployer and said operating member, said handle including a hand grip for operating said deployer and a finger grip for operating said operating member independently of said deployer, said operating member including an elongate, hollow knotting element pusher having a longitudinal axis and a plurality of push fingers disposed around said axis, said knotting element pusher having an initial longitudinal position wherein said push fingers are disposed in a contracted position proximally of a knotting element of an externally deployed ligature loop, said push fingers in said contracted position being disposed close to said axis for engaging said knotting element of the externally deployed ligature loop, said knotting element pusher being movable longitudinally, distally from said initial position to an extended longitudinal position with said push fingers in said contracted position to move said knotting element of the externally deployed ligature loop in said direction to contract the externally deployed ligature loop to form a ligature, said instrument body further including an engaging member for holding said ligature material as said knotting element of the eternally deployed ligature loop is moved by said knotting element pusher in said direction, said engaging member including an elongate, hollow jaw member including a pair of opposed jaws disposed within said knotting element pusher when said knotting element pusher is in said initial and extended positions, said jaws being in a closed position when said knotting element pusher is in said initial and extended positions, said jaws in said closed position holding said ligature material therebetween.

16. A ligating instrument as recited in claim 15 wherein said knotting element pusher is movable longitudinally, proximally from said initial position to a retracted position wherein said push fingers are in an expanded position, said push fingers in said expanded position being disposed further away from said axis, said jaws being movable from said closed position to an open position when said knotting element pusher is in said retracted position, said jaws in said open position releasing said ligature material.

17. A ligating instrument as recited in claim 16 wherein said deployer includes an elongate plate disposed in said jaw member and releasably engaging said ligature supply, said plate having a neutral longitudinal position wherein a distal end of said plate is disposed within said jaw member with said jaws in said closed position, said plate being movable longitudinally, distally relative to said jaw member from said neutral position to a deployed longitudinal position to move said jaws to said open position with said knotting element pusher in said retracted position, said distal end of said plate in said deployed position being disposed externally of said jaws and said push fingers such that one of said ligature loops is moved externally of said jaws and said push fingers, said plate being movable longitudinally, proximally relative to said jaw member from said deployed position to said neutral position to release said one ligature loop externally of said instrument body.

18. A ligating instrument as recited in claim 17 wherein said hand grip includes a squeezable hand grip for moving said plate relative to said jaw member.

19. A ligating instrument as recited in claim 18 wherein said handle includes a locking mechanism for selectively, releasably locking said hand grip in a squeezed position.

20. A ligating instrument as recited in claim 19 wherein said finger grip includes first and second push buttons biased longitudinally relative to said hand grip, said first push button being depressible relative to said hand grip in a first direction for moving said knotting element pusher to said extended position and said second push button being depressible relative to said hand grip in a second direction for moving said knotting element pusher to said retracted position.

21. A ligating instrument as recited in claim 20 wherein said ligature supply is formed entirely of said filamentous ligature material, said knotting elements include slidable knots formed from said ligature material, said ligature loops are connected to one another by connecting segments of said ligature material, and said instrument body further includes means for cutting said connecting segment of an externally deployed ligature loop to sever a ligature formed with the externally deployed ligature loop from the remainder of said ligature supply.

22. A ligating instrument as recited in claim 21 wherein said cutting means includes a cutting edge carried by said jaw member.

23. A ligating instrument for forming ligatures in anatomical structure at an internal operative site in a body comprising
    an elongate pusher having a distal end for being introduced at the operative site, a proximal end and a lumen between said distal and proximal ends, said distal end being movable from a contracted position to an expanded position; and
    an actuator disposed in said lumen and releasably carrying a ligature supply including a plurality of preformed, contractible ligature loops formed of a continuous length of filamentous ligature material, said ligature loops having knotting elements movable along said ligature material in a direction to contract said ligature loops around anatomical structure, said knotting elements having a size preventing passage of said ligature loops through said distal end in said contracted position and permitting passage of said ligature loops through said distal end in said expanded position, said pusher being movable relative to said actuator to move said distal end from said contracted position to said expanded position and back to said contracted position, said actuator being movable relative to said pusher when said pusher is in said expanded position to release at least one of said ligature loops externally of said distal end, said pusher being movable back to said contracted position after said at least one ligature loop has been released externally of said distal end, said pusher in said contracted position being movable longitudinally along said ligature material to move said knotting element of said at least one ligature loop in said direction to contract said at least one ligature loop around anatomical structure to form a ligature.

24. A ligating instrument as recited in claim 23 wherein said pusher is biased longitudinally relative to said actuator to be disposed in an initial longitudinal position wherein said distal end is disposed in said contracted position, said pusher being movable from said initial position longitudinally, distally relative to said actuator to an extended longitudinal position to move said knotting element of said at least one ligature loop in said direction to contract said at least one ligature loop, said pusher being movable longitudinally, proximally relative to said actuator from said extended position back to said initial position, said pusher being movable from said initial position longitudinally, proximally relative to said actuator to a retracted position to move said distal end from said contracted position to said expanded position to allow said actuator to release another one of said ligature loops externally of said distal end.

25. A ligating instrument as recited in claim 24 wherein said actuator has a neutral longitudinal position wherein a distal end of said actuator is disposed within said pusher when said pusher is in said initial position, said actuator being movable longitudinally, distally relative to said pusher from said neutral position to a deployed longitudinal position when said pusher is in said retracted position to position said distal end of said actuator externally of said distal end of said pusher.

26. A ligating instrument for forming ligatures in anatomical structure at an internal operative site in a body comprising an elongate pusher having a distal end for being introduced at the operative site, a proximal end and a lumen between said distal and proximal ends, said distal end being movable from a contracted position to an expanded position; and an actuator disposed in said lumen and releasably carrying a ligature supply including a plurality of performed, contractible ligature loops of filamentous ligature material, said ligature loops having knotting elements movable along said ligature material in a direction to contract said ligature loops around anatomical structure, said knotting elements having a size preventing passage of said ligature loops through said distal end in said contracted position and permitting passage of said ligature loops through said distal end in said expanded position, said pusher being movable relative to said actuator to move said distal end from said contracted position to said expanded position and back to said contracted position, said actuator being movable relative to said pusher when said pusher is in said expanded position to release at least one of said ligature loops externally of said distal end, said pusher being movable back to said contracted position after said at least one ligature loop has been released externally of said distal end, said pusher in said contracted position being movable longitudinally along said ligature material to move said knotting element of said at least one ligature loop in said direction to contract said at least one ligature loop around anatomical structure to form a ligature, said pusher being biased longitudinally relative to said actuator to be disposed in an initial longitudinal position wherein said distal end is disposed in said contracted position, said pusher being movable from said initial position longitudinally, distally relative to said actuator to an extended longitudinal position to move said knotting element of said at least one ligature loop in said direction to contract said at least one ligature loop, said pusher being movable longitudinally, proximally relative to said actuator from said extended position back to said initial position, said pusher being movable from said initial position longitudinally, proximally relative to said actuator to a retracted position to move said distal end from said contracted position to said expanded position to allow said actuator to release another one of said ligature loops externally of said distal end, said actuator having a neutral longitudinal position wherein a distal end of said actuator is disposed within said pusher when said pusher is in said initial position, said actuator being movable longitudinally, distally relative to said pusher from said neutral position to a deployed longitudinal position when said pusher is in said retracted position to position said distal end of said actuator externally of said distal end of said pusher, said knotting elements being connected to one another by segments of said ligature material, said actuator including a retention member releasably engaging said ligature supply, said ligature supply being movable distally with said actuator when said actuator is moved to said deployed position to position a distal most one of said ligature loops externally of said distal end of said pusher, said actuator being movable proximally from said deployed position to said neutral position to release said ligature supply such that said distal most ligature loop is released externally of said distal end of said pusher, said knotting element of said distal most ligature loop being disposed distally of said distal end of said pusher when said pusher is moved back to said initial position, said retention member releasably reengaging said ligature supply when said actuator is moved from said neutral position to said deployed position to deploy another one of said ligature loops.

27. A ligating instrument as recited in claim 26 wherein said actuator includes an elongate plate and said retention member extends distally from said plate to define a recess for receiving said knotting elements of said ligature loops.

28. A ligating instrument as recited in claim 27 wherein said actuator includes a plurality of retention members for releasably engaging said knotting elements.

29. A ligating instrument for forming ligatures in anatomical structure at an internal operative site in a body comprising an elongate member having a distal end for being introduced at the operative site, a proximal end and a lumen between said distal and proximal ends, said distal end being movable from a closed position to an open position;

a ligature supply disposed in said lumen including a continuous length of filamentous ligature material forming a plurality of preformed, contractible, closed ligature loops and connecting segments extending between said ligature loops and structurally connecting said ligature loops to one another in series, said ligature loops having knotting elements movable along said ligature material in a direction to contract said ligature loops around anatomical structure, said knotting elements being of a size preventing passage of said ligature loops through said distal end in said closed position and permitting passage of said ligature loops through said distal end in said open position;

an actuator for moving said distal end from said closed position to said open position, said actuator being disposed in engagement with said ligature material to move one of said ligature loops through said distal end when said distal end is moved to said open position by said actuator whereby said one ligature loop is positioned externally of said elongate member; and an operating member movable relative to said elongate member and along said ligature material to move said knotting element of said one ligature loop in said direction to contract said one ligature loop around anatomical structure to form a ligature.

30. A ligating instrument as recited in claim 29 wherein said knotting elements are connected to one another by said connecting segments and said connecting segment connecting said knotting element of said one ligature loop to said knotting element of a next proximal ligature loop passes through said distal end in said closed position when said one ligature loop is positioned externally of said elongate member, said distal end of said elongate member including opposed edges for holding said connecting segment of said one ligature loop between said edges when said operating member is moved along said ligature material to move said knotting element of said one ligature loop to contract said one ligature loop.

31. A ligating instrument for forming ligatures in anatomical structure at an internal operative site in a body comprising an elongate member having a distal end for being introduced at the operative site, a proximal end and a lumen between said distal and proximal ends, said distal end being movable from a closed position to an open position;

a ligature supply disposed in said lumen including a plurality of preformed, contractible ligature loops of filamentous ligature material, said ligature loops having knotting elements movable along said ligature material in a direction to contract said ligature loops around anatomical structure, said knotting elements being of a size preventing passage of said ligature loops through said distal end in said closed position and permitting passage of said ligature loops through said distal end in said open position;

an actuator for moving said distal end from said closed position to said open position, said actuator being disposed in engagement with said ligature material to move one of said ligature loops through said distal end when said distal end is moved to said open position by said actuator whereby said one ligature loop is positioned externally of said elongate member; and an operating member movable along said ligature material to move said knotting element of said one ligature loop in said direction to contract said one ligature loop around anatomical structure to form a ligature, said knotting elements being connected to one another by connecting segments of said ligature material and said connecting segment connecting said knotting element of said one ligature loop to said knotting element of a next proximal ligature loop passes through said distal end in said closed position when said one ligature loop is positioned externally of said elongate member, said distal end of said elongate member including opposed edges for holding said connecting segment of said one ligature loop between said edges when said operating member is moved along said ligature material to move said knotting element of said one ligature loop to contract said one ligature loop, one of said opposed edges including a cutting edge segment joined to a grasping edge segment thereof for cutting said connecting segment of said one ligature loop to separate the ligature from the remainder of said ligature supply.

32. A ligating instrument as recited in claim 31 wherein said actuator is disposed in said lumen, and said actuator is movable longitudinally, distally relative to said elongate member to a deployed longitudinal position to move said distal end from said closed position to said open position, said actuator having a distal end disposed within said distal end of said elongate member in said closed position and disposed externally of said distal end of said elongate member in said deployed position, said actuator including retention members extending longitudinally in said lumen, said retention members releasably holding said knotting elements to move said knotting elements distally when said actuator is moved to said deployed position, a distal most one of said retention members being disposed externally of said elongate member when said actuator is in said deployed position such that, when said knotting element of said one ligature loop is held by said distal most retention member, said one ligature loop is positioned externally of said distal end of said elongate member, said actuator being movable proximally from said deployed position relative to said elongate member to release said knotting elements whereby said knotting element of said one ligature loop is released externally of said elongate member and said one retention member engages and holds said knotting element of said next proximal ligature loop disposed within said lumen.

33. A ligating instrument as recited in claim 32 wherein said operating member includes an elongate member having a distal end, a proximal end and a lumen between said distal end of said operating member and said proximal end of said operating member and said elongate member is disposed in said lumen of said operating member.

34. A method of forming ligatures in anatomical structure at an internal operative site in a body comprising the steps of introducing a distal end of an elongate member of a ligating instrument at an internal operative site;

moving the distal end from a contracted position to an expanded position;

moving an actuator of the ligating instrument to distally advance a continuous length of filamentous ligature material within a lumen of the elongate member to correspondingly advance a plurality of preformed, structurally interconnected, contractible, closed ligature loops formed by the ligature material within the lumen of the elongate member to move one of the ligature loops externally of the distal end in the open position;

positioning the external ligature loop around anatomical structure to be ligated; and moving a knotting element pusher of the ligating instrument relative to the elongate member to move a knotting element of the external ligature loop to contract the external ligature loop around the anatomical structure to form a ligature.

35. A method of forming ligatures as recited in claim 34 wherein said step of moving the distal end from the closed position to the open position and said step of moving the actuator to distally advance the ligature material and the ligature loops includes moving the actuator longitudinally relative to the elongate member.

36. A method of forming ligatures as recited in claim 35 wherein said step of moving the actuator to advance the ligature material and the ligature loops includes the step of releasably engaging the ligature loops with the actuator.

37. A method of forming ligatures as recited in claim 36 and further including, subsequent to said step of moving the actuator to advance the ligature material and the ligature loops, the step of moving the actuator relative to the ligature material to disengage the ligature loops from the actuator.

38. A method of forming ligatures as recited in claim 37 wherein said step of moving the knotting element pusher includes moving the knotting element pusher relative to the actuator and along the ligature material in the direction of the anatomical structure to move the knotting element of the external ligature loop along the ligature material.

39. A method of forming ligatures in anatomical structure at an internal operative site in a body comprising the steps of introducing a distal end of an elongate member of a ligating instrument at an internal operative site;

moving the distal end from a contracted position to an expanded position;

moving an actuator of the ligating instrument to distally advance a plurality of preformed, contractible ligature loops of filamentous ligature material within a lumen of the elongate member to move one of the ligature loops externally of the distal end in the open position, the ligature loops being connected to one another by segments of the ligature material;

positioning the external ligature loop around anatomical structure to be ligated;

moving a knotting element of the external ligature loop to contract the external ligature loop around the anatomical structure to form a ligature; and cutting the segment of ligature material of the external ligature loop to sever the ligature from the remainder of the ligature loops.

40. A method of forming ligatures as recited in claim 39 and further including, during said step of moving the knotting element, the step of holding the segment of ligature material of the external ligature loop.

41. A method of forming ligatures as recited in claim 40 and further including, subsequent to said step of cutting, repeating the steps of moving the distal end from the closed position to the open position and moving the actuator to advance the ligature loops to deploy another ligature loop externally of the elongate member for use in forming another ligature without withdrawing the distal end of the elongate member from the operative site.

42. A method of forming ligatures as recited in claim 41 wherein said step of repeating said step of moving the actuator to advance the ligature loops includes releasably reengaging the another ligature loop with the actuator.

* * * * *